US006008264A

United States Patent [19]

Ostler et al.

[11] Patent Number: 6,008,264

[45] Date of Patent: Dec. 28, 1999

[54] METHOD FOR CURING POLYMERIC MATERIALS, SUCH AS THOSE USED IN DENTISTRY, AND FOR TAILORING THE POST-CURE PROPERTIES OF POLYMERIC MATERIALS THROUGH THE USE OF LIGHT SOURCE POWER MODULATION

[75] Inventors: Calvin D. Ostler; Kevin D. Ostler, both of Riverton; David W. Kaufman, Salt Lake City, all of Utah

[73] Assignee: Laser Med, Inc., Salt Lake City, Utah

[21] Appl. No.: 09/067,084

[22] Filed: Apr. 27, 1998

Related U.S. Application Data

[60] Provisional application No. 60/045,140, Apr. 30, 1997.

[51] Int. Cl.[6] .......... C08F 2/46

[52] U.S. Cl. .......... 522/4; 522/908; 433/29; 427/492; 427/493; 523/116

[58] Field of Search .......... 522/908, 4; 433/29, 433/215; 427/492, 493; 523/115, 116

[56] References Cited

U.S. PATENT DOCUMENTS

| | | | |
|---|---|---|---|
| 3,943,046 | 3/1976 | DeSorga et al. | 204/159.23 |
| 4,329,421 | 5/1982 | Wisnoky et al. | 430/322 |
| 4,411,931 | 10/1983 | Duong | 427/54.1 |
| 5,007,837 | 4/1991 | Werly | 433/226 |

*Primary Examiner*—James J. Seidleck
*Assistant Examiner*—Sanza McClendon
*Attorney, Agent, or Firm*—Daniel McCarthy

[57] ABSTRACT

A method and system are disclosed for curing polymeric materials including dental composites. Preferably, modulated light is used to control the formation of polymer chains in the polymeric material so that a cured polymeric material that has the desired physical characteristics for its intended function. Formation of short chain and long chain polymers from monomers in the polymeric material is initiated and controlled by using a light source with a wavelength suitable for one or more initiators found in the polymeric material.

47 Claims, 14 Drawing Sheets

BASELINE SCENARIO

METHOD FOR CURING POLYMERIC MATERIALS, SUCH AS THOSE USED IN DENTISTRY, AND FOR TAILORING THE POST-CURE PROPERTIES OF POLYMERIC MATERIALS THROUGH THE USE OF LIGHT SOURCE POWER MODULATION

Priority is hereby claimed to United States provisional patent application serial no. 60/045,140 which was filed on Apr. 30, 1997.

I. BACKGROUND OF THE INVENTION

A. Field of the Invention

This invention relates to the use of light sources to cure polymeric materials, particularly those used in dentistry, and through that curing to tailor the post-cure properties of the materials in order to achieve desired physical properties in the materials. The invention includes various modulation schemes for causing polymeric materials to cure in a desired manner.

B. The Background Art

In the prior art, curing dental materials by the use of light was known. For example, U.S. Pat. No. 5,472,991, which is hereby incorporated by reference, discloses a dental composition that can be polymerized by the use of two curing steps using light of different wavelengths during the two steps. U.S. Pat. No. 5,350,834, which is hereby incorporated by reference, discloses photoinitiated control of inorganic network formations in the sol-gel process. U.S. Pat. No. 4,872,936, which is hereby incorporated by reference, discloses photocuring of mixtures which could be used in dentistry or medicine. Other patents to which the reader may wish to refer to understand the background against which the invention was made are U.S. Pat. Nos. 4,191,622, 4,224,525, 4,273,335, 4,298,005, 5,002,854, 5,002,855, 5,154,861, and 5,175,077, each of which is hereby incorporated by reference.

II. SUMMARY OF THE INVENTION

In the field of dentistry, there is a significant trend away from use of metal materials for repair and reconstruction of teeth and the construction of dental appliances. Dentists and dental technicians are now relying on polymeric materials for applications which in the past required the use of metals. Polymeric materials are preferred by many dentists due to their ease of formation, superior aesthetic results, and avoidance of concerns about release of mercury from amalgams used in other dental restorative materials.

Polymeric dental materials can be very durable if prepared and cured properly. In particular, the polymerization process that the materials undergo should be tailored to provide a hard and durable resulting dental appliance or reconstruction, but should not exhibit brittleness, stress cracking, shrinkage or other undesirable qualities. The particular application of a dental material requires that it has physical characteristics tailored to that application in order to maximize performance.

It is an object of the invention to provide a method and system for curing polymeric dental materials. It is a feature of a preferred embodiment of the invention that various lasers are used to cure polymeric dental materials. It is a consequent advantage of the invention that the dental materials may be cured quickly and to a predetermined physical state.

It is an object of the invention to provide a method and system for tailoring the post-cure properties of dental materials. It is a feature of the invention that light is applied to the dental materials to cause their polymerization and cure.

It is an object of the invention to tailor the post cure properties of dental materials. It is a feature of the invention that light is applied to the dental materials according to various power, wave form and modulation parameters in order to cause the particular dental materials to cure into a final form with desired properties. It is a consequent advantage of the invention that the performance of the dental materials may be optimized for a particular application or environment by curing techniques.

It is an object of the invention to utilize a light power source in order to cure dental materials on an intermittent or sporadic basis so that a single light power source may serially provide power to several physically discrete quantums of dental materials to be cured. It is a feature of the invention that some preferred embodiments of the invention involve applying light to a dental material in a periodic fashion such as on/off, so that while a first dental material is experiencing the off-phase of its cure, the light power source may be used to provide light and power to the on-phase of a second dental material to be cured. It is an advantage of the invention that in a dental office having several dentists or technicians, multiple dental material curing lights could be powered for simultaneous use by a single light power source, reducing the cost of the capital investment in equipment.

It is an object of the invention to affect the growth of polymer chains in polymeric dental materials. It is a feature of the invention that light source power modulation is employed in order to initiate and control the growth of polymer chains in polymeric dental materials so that the resulting materials have chains of a desired length, resulting a cured dental material with desired strength, hardness, lack of brittleness and other properties desired for its particular use.

It is an object of the invention to provide a light source power modulation scheme that minimizes shrinkage of a dental material during cure. It is a feature of the invention that light may be first applied to the dental material at high power level, dropped over time to a lower power level and then maintained at the lower power level. It is an advantage of the invention that such a modulation scheme minimizes shrinkage in a dental material.

It is an object of the invention to provide a light source power modulation scheme that creates a post-cure dental material that is flexible. It is a feature of the invention that light may be applied to the dental material at a first power level, held constant at that first power level for a period of time, and then increased over time to a second power level. It is an advantage of the invention that such a modulation scheme produces flexibility in a dental material.

It is an object of the invention to provide a light source power modulation scheme that creates a post-cure dental material that has great surface or wear strength. It is a feature of the invention that light may be applied to the dental material at a first high power level, quickly reduced to a lower power level, and then gradually increased to about the first high power level again. It is an advantage of the invention that such a modulation scheme produces significant surface or wear strength in a dental material.

It is an object of the invention to provide a light source power modulation scheme that creates a post-cure dental material that is useful as a pit and fissure sealant. It is a feature of the invention that light may be applied to the dental material at a first high power level, decreased to a second lower power level, and then held constant at about that second power level for a period of time. It is an advantage of the invention that such a modulation scheme produces a dental material that has the qualities needed to serve as a pit and fissure sealant.

It is an object of the invention to provide a light source power modulation scheme that creates a post-cure dental material that is useful as a bonding agent for indirect applications. It is a feature of the invention that light may be applied to the dental material in an increasing and decreasing pattern according to a sine wave, particularly initiating light exposure at a mid-power level on the sine wave. It is an advantage of the invention that such a modulation scheme produces a dental material that has characteristics suitable for use as a bonding agent for indirect applications.

It is an object of the invention to provide a light source power modulation scheme that creates a post-cure dental material that is useful as a bonding agent for direct applications (such as orthodontics). It is a feature of the invention that light may be applied to the dental material according to a discontinuous waveform. For example, the waveform may include initiating power and holding it constant for a period of time at a first low power level, turning power to the light source off for a period of time, and then reinitiating power and holding it constant for a period fo time at a second higher power level. It is an advantage of the invention that such a modulation scheme produces a dental material useful as a bonding agent for orthodontic applications.

Many other modulation schemes and tailoring the post-cure characteristics of the dental material or other polymeric material for almost any use are possible within the inventive concept. Other objects, features and advantages of the invention will become apparent to persons of ordinary skill in the art upon reading the specification and reviewing the appended figures.

III. BRIEF DESCRIPTION OF THE DRAWINGS

IV. DETAILED DESCRIPTION OF THE INVENTION

A. General Description

Figure 1:
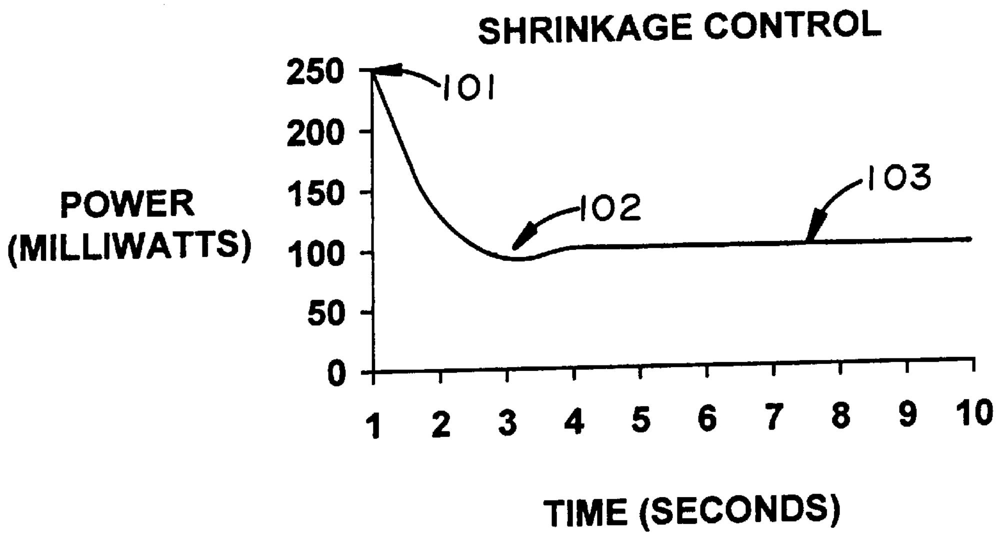
FIGS. 1–6 depict examples of light source modulation for curing composite materials.

The intended placement and use of a dental material affect the properties that will be desired from the material. For some dental applications, a softer and more flexible dental material is desired, and for others a harder and less flexible dental material is desired. Thus, it is important to be able to cure a polymeric dental material into a finished form with physical qualities suited for the specific function that the dental material will perform in a given patient.

In general, short polymer chains can be very hard, but they lack flexibility. Long polymer chains tend to be more flexible, but it takes them longer to form. As the longer chains form, the dental material tends to move around resulting in gaps between a tooth on which the dental materials are placed and the dental materials. The length of the polymer chains is related to how long free radical complexes can link monomers together before encountering another free radical complex. When two free radical complexes encounter each other, a bond is formed between them and the polymer-forming reaction is terminated. If this happens quickly, short chains are formed. If this happens slowly, long chains are formed. The chemical reactions being described for polymer formation are photo-initiated free radical chain reactions. A photo-initiated free radical is formed when it absorbs light energy of the appropriate wavelength. If a high amount of light energy is applied to the material, then a high number of free radicals will be formed, they will encounter and contact each other often and consequently short polymer chains are formed. If a low amount of light energy is applied to the material, few radicals will form and long polymer chains will result. The speed at which radicals in these reactions encounter each other is algebraically proportional to the concentration of the free radical formed and is described in physical chemical kinetics as the "Termination Rate". A specific example of this is diketone photo-initiated free radical polymerization which exhibits second order chemical kinetics. This means that the Termination Rate is directly proportional to the square of the concentration of free radical initially formed by absorbing light of the appropriate wavelength. Because of this algebraic relationship small changes in the amount of light being applied can produce significant changes in how many short chain, medium length chains and long chains form as the material is curing. The specific mixture or ratio of these chain lengths govern the post-cure physical properties. By selecting the amount of light energy applied to the material, the length of chains to be formed can be selected. By adjusting or modulating the amount of light energy applied to a polymeric material at selected times during the polymerization reaction, both the length of the polymer chains and the concentration of long chains to short chains in the resulting material may be controlled. This allows the precise physical properties of the resulting material to be achieved by controlling the polymerization reaction.

There are many variables at work which influence the properties of a material after the polymerization reaction is complete. These include the polymeric material that is started with, the nature of the light, the power of the light, the duration that the light is applied to the polymeric material, modulation of the light, and others. Control of the variables is important in order to achieve the desired result.

Some of the issues that should be considered when working with polymeric dental materials include shrinkage, flexural strength and surface or wear strength. Combinations of properties addressing these issues are desired when creating pit and fissure sealants, bonding agents, and orthodontic adhesives.

For the purposes of this document, the reader should be familiar with some terms. As used herein, "polymeric" means any material that cures by converting monomers and/or their derivatives (i.e. olgimers) into polymers. Restorative dental compound means a polymeric material that is used as a direct restorative material to fill cavities or rebuild teeth. Dental material means any polymeric material that is used in dentistry. Composite means a mixture that includes monomers and/or their derivatives (i.e. olgimers), and may also include dyes, filler materials, photo-initiator(s) and solvent(s). Cure means applying the appropriate wavelength of light to accelerate an initiator into a free radical state which, in turn converts monomers and/or their derivatives (i.e. olgimers) into polymers. Modulate means to vary intensity or power over time, such as in on/off, high/low, increase/decrease, combinations of these and other power adjustments. Dental surface means any surface of a tooth or dental appliance. This includes cutting surfaces (incisal), chewing surfaces (occlusal), vertical surfaces facing outward toward the face (facial), vertical surfaces facing inward toward the tongue (lingual), vertical surfaces facing toward the front of the head (mesial), vertical surfaces facing toward the back of the head (distal). "Poly Chromatic Acusto Optic Modulator" means a device that by receiving either various input frequencies or acoustical waves separates and/or mixes and/or eliminates different wavelengths of light from a multiple wavelength light source. "Current Frequency" or "Frequency" means the number of times per second the electrical current charge for a positive (+) charge to a negative (−) charge (i.e, the frequency of 60 hertz changes from positive to negative 60 times per second).

B. Direct Restorative Dental Composites

1. Shrinkage

A major concern in restorative dentistry is the shrinkage of a resin when it is cured. Once the cavity has been prepared, the composite is placed at or in the location of the tooth where tooth material had been removed and needs to be replaced. The composite is then cured. If the resin shrinks as it is cured, it will pull away from the tooth surface leaving a gap between the tooth and the resin. The gap provides a space where bacteria can leak past the restoration and cause an infection.

When curing dental material used to repair a cavity, by first applying a rapid influx of light energy (a high energy level), a matrix of short chain polymers may be set in the composite dental material very quickly. This matrix or "set" provides a rigid structure within the composite that reduces shrinkage. Once the short chain polymer matrix is formed, the amplitude of light energy can be reduced to a much lower level and held constant or otherwise adjusted. The lower level of light energy permits the remaining polymers to form long chains which can be used to provide flexibility or flexural strength in the polymerized dental material. Referring to FIG. 1, a graph is provided which illustrates one example of light power modulation with the intention of controlling or minimizing shrinkage of the dental material. The graph shows that initially light power is applied at a high level at 101. The particular high level used in the example is 250 milliwatts. In the example, immediately upon application of the high power level it is continuously decreased to a desired point and then kept constant over time. The period of decrease in the example is about 3.5 seconds. Then the power is stabilized at a lower level 102, such as 100 milliwatts. The lower level in the example is 40% (or less than half) of the initial power level. Power is then maintained at a constant level 103, such as 100 milliwatts, for an additional period of time (6.5 seconds or more in the example). Note that this is approximately twice the time period of the power decrease period in the example, but could be any appropriate time period. The precise amount of time that light at high power is applied to the dental material, the way the power is reduced, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 1.

2. Flexural Strength

Figure 2:
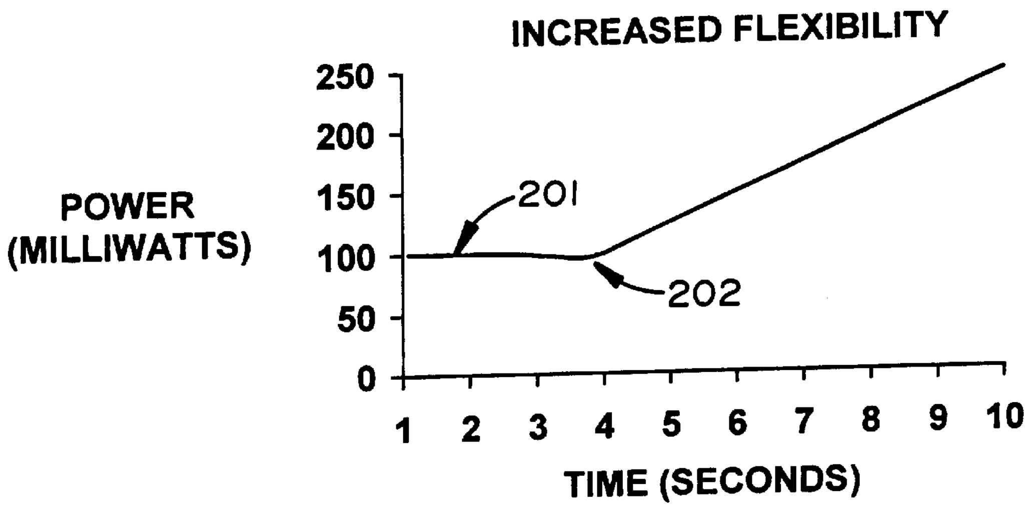

In certain restorations, in particular those that are on the chewing surfaces (occlusal surfaces) of the teeth, flexural strength is the post cure physical property of the dental material of most concern. For this application it is preferred that the material form the longest polymer chains possible in order to maximize flexibility. Referring to FIG. 2, a graph is depicted which indicates how it is preferred to modulate light power over time in order to maximize flexural strength of the dental material. As depicted in the graph, light power is initially kept at a constant level 201 (such as 100 milliwatts) for a period of time (such as 4 seconds) and then progressively increased over time 202. Note that in the example, the ending power level is about 2.5 times the initial constant power level. The precise amount of time that light is maintained at the constant power level, the way (rapidly, slowly or variably) the power is increased, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 2.

3. Surface or Wear Strength

Figure 3:
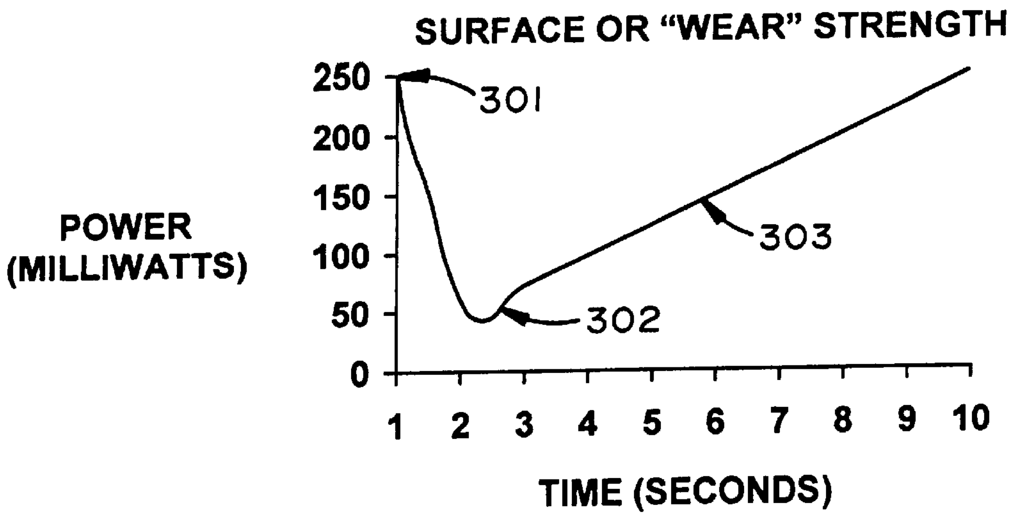

In some dental applications such as cutting surfaces (incisal surfaces), surface or wear strength of the material is of primary concern. In such an instance, modulation of light generally like that depicted in FIG. 3 tends to maximize surface or wear strength. That includes application of instantaneous high power 301 to produce strong short polymer chains on the surface of the dental material, reducing power over time to a low light source power level 302 which causes long chains to form deep in the dental material, followed by increasing the light power level over time 303 and ending at a high power level in order to finish polymerizing the dental material. The precise amount of power at various times during the curing process, the precise amount of curing time, the exact way the power is decreased and increased, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 3.

C. Pit and Fissure Sealants

Figure 4:
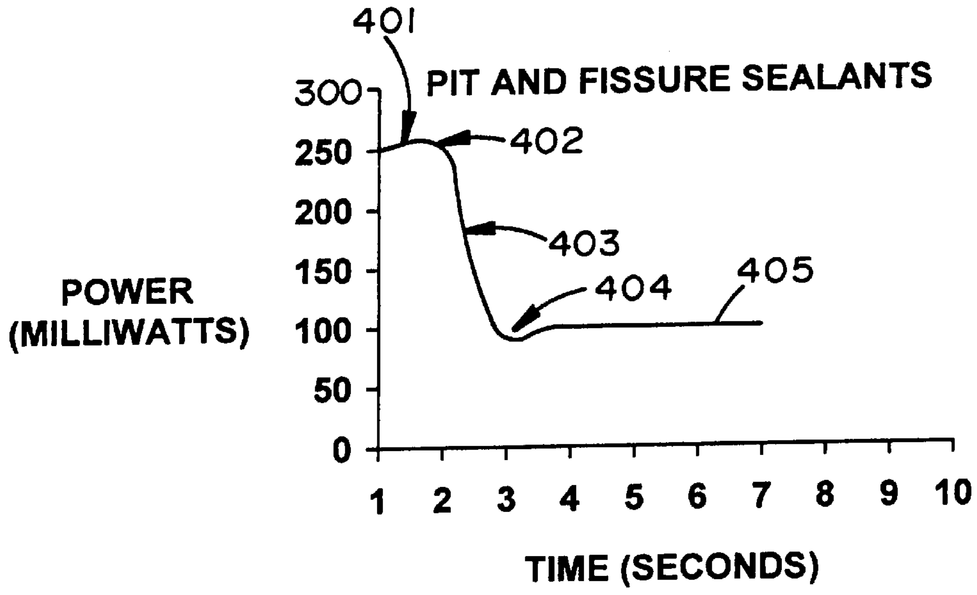

Pit and fissure sealants require strong surface or wear strength but also must shrink around the tooth for a tight fit. Referring to FIG. 4, a graph is provided which depicts light source power modulation in order to provide optimum polymerization of a dental material for use as a pit or fissure sealant. Initially light power is applied at a high level 401 and increased some over time 402, then rapidly dropped 403 to a lower level 404, increased slightly and then kept constant 405 over time until the dental material is cured or fully polymerized. The precise amount of power at various times during the curing process, the precise amount of curing time, the exact way the power is modulated, the precise power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 4.

D. Bonding Agents for Indirect Applications

Figure 5:
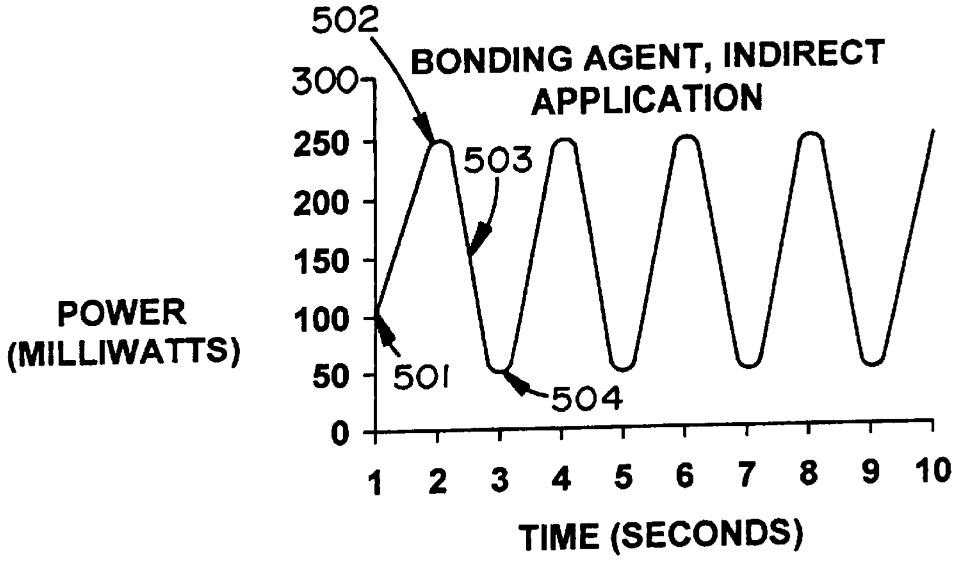

Bonding agents for indirect applications, such as crowns, bridges and veneers require maximum adhesion and flexibility, but face the unique problem that light energy must pass through the indirect restoration (crown, bridge, etc.) in order to reach the dental material to be polymerized. Referring to FIG. 5, a graph is depicted which is an example of light power source modulation requisite to penetrate the indirect restoration to start a slow polymerization reaction 501 (e.g., 100 milliwatts), increased according to a sine function to a high power level 502 (such as 250 milliwatts, and decreased 503 according to a sine function to a low power level 504 (such as 50 milliwatts), which allows the reaction to proceed and build long polymer chains. The light source power is then increased and decreased periodically according to a sine function and the cycle may be repeated more than once but perhaps many times in order to fully polymerize the dental material (i.e., in order to convert most or the majority of monomers in the dental material to polymers). The precise amount of power at various times during the curing process, the precise amount of curing time, the exact way the power is modulated, the precise power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 5.

E. Bonding Agents for Other Applications

Figure 6:
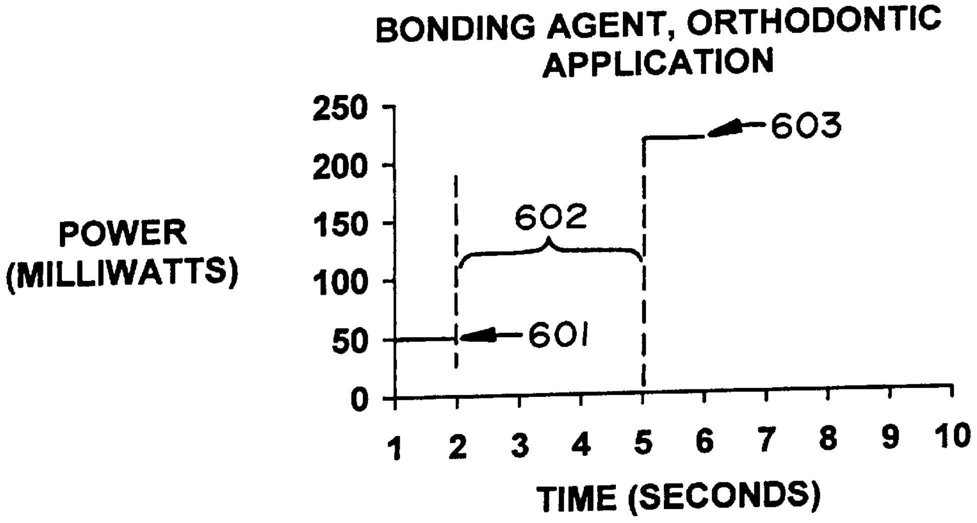

Bonding agents for other applications, such as orthodontic applications, must strongly but temporarily affix orthodontic brackets to the enamel of teeth. The dental material used for this purpose should be strong enough to withstand the rigors of orthodontic treatment but brittle enough so that when the orthodontic treatment is concluded, the dental material may be shattered or broken in order to remove the orthodontic bracket without removing enamel from the tooth. Referring to FIG. 6, a graph is depicted which shows an example of light source power modulation in order to cure a polymeric dental material to have physical characteristics desirable for bonding agents for direct applications such as orthodontic brackets. As depicted in the graph, polymerization or cure is begun 601 with the light source at a low power for a period of time (1 second in the example). This initiates long chain polymer growth. The light source is then terminated. In the example, the light source is terminated for a time 602. Then light is reinitiated at a high power level 602 for a brief period of time (1 second in the example) in order to cause the desired brittleness in the dental material. The discontinuous nature of the power modulation curve is believed to work best for curing dental materials for orthodontic applications.

The precise amount of power at various times during the curing process, the precise amount of curing time, the exact way the power is modulated, the precise power levels, and the total time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and light source application depicted in FIG. 6.

F. Types of Dental Materials

The preferred dental material used in the various embodiments of this invention and variations of those embodiments is a polymeric dental material that includes monomer(s) (which may be of various concentrations and type), initiator (s), fill material, dyes and solvent(s). Such a dental material is polymerized by exposing it to a light source of a wavelength that causes the initiator to start and carry out polymerization of the monomers into polymers of desired lengths. The light source must be matched with the initiator so that the light source is of a wavelength that initiates and carries out the polymerization reaction.

For reference, Table I below shows various initiators (initiators) and the wavelength of light to which each is sensitive. Any of these or other initiators may be used in the invention.

TABLE I

| Initiator | Wavelength |
|---|---|
| 2-Isopropylthioxanthone | 258 nm |
| 2-tert-Butylthioxanthone | 259 nm |
| 2-Phenylthioxanthone | 267 nm |
| 2-Benzylthioxanthone | 260 nm |
| 2 Cyclohexylthioxanthone | 259 nm |
| 4-Isopropylthioxanthone | 262 nm |
| 2-Acetylthioxanthone | 255 nm |
| 2-Chloroxanthone | 240 nm |
| Fluorenone | 247 and 257 nm |
| Dibenzosuberone | 215 and 268 nm |
| 6,11-Dihydrodibenzo-thiepin-11-one | 239 nm |
| 2-Chloro-6,11-dihydrodibenzo-thiepin-11-one | 241 nm |
| Thioxanthone | 255 nm |
| 2-Chlorothioxanthone | 260 nm |
| 2-Methylthioxanthone | 258 nm |
| 2-Ethylthioxanthone | 258 nm |
| Benzoin Methyl Ether | 323 nm |
| 2,2-Dimethoxy-2-phenyl acetophenone | 335 nm |
| 2-Hydroxycyclohexane acetophenone | 320 nm |
| 1-Hydroxycyclohexane acetophenone | 326 nm |
| 2,2-Diethoxy acetophenone | 323 nm |
| Darocure-1116 | 313 nm |
| Darocure-1664 | 383 nm |
| Darocure-2273 | 383 nm |
| Thioxanthne-9-one | 378 nm |
| Camphorquinone | 467 nm |

Also for reference, in Table II below a list of various commercially-available dental materials and their source is provided.

TABLE II

| NAME | MANUFACTURER |
|---|---|
| MICROFILLED 0.04 MICRONS | |
| Durafill VS | Kulzer, Germany |
| Heliomolar | Vivadent, Liechtenstein |
| Helioprogress | Vivadent, Liechtenstein |
| Perfection | Den-Mat, Santa Maria, CA |
| Prisma Microfine | Caulk/Dentsply, Milford, DE |
| Renamel | Cosmedent, Germany |
| Silux Plus | 3M, St. Paul, MN |
| Visio Dispers | ESPE/Premier, Norristown, PA |
| SMALL PARTICLE 1–5 MICRONS | |
| Estilux | Kulzer, Germany |
| Estilux C | Kulzer, Germany |
| Paste Laminate | Den-Mat, Santa Maria, CA |

TABLE II-continued

| NAME | MANUFACTURER |
|---|---|
| Prisma Fill | Caulk/Dentsply, Milford, DE |
| Valux | 3M, St. Paul, MN |
| Visiofil | ESPE/Premier, Norristown, PA |
| HYBRID 0.04 + 5 MICRONS | |
| Prisma APH | Caulk/Dentsply, Milford, DE |
| Bisfil M | Bisco, Itasca, IL |
| Bisfil P | Bisco, Itasca, IL |
| Command Ultrafine | Kerr, Orange, CA |
| Conquest | Jeneric/Pentron, Wallingford, CT |
| Herculite | Kerr, Orange, CA |
| Multi-fil | Kulzer, Germany |
| P-50 | 3M, St. Paul, MN |
| Pentra-fil II | Jeneric/Pentron, Wallingford, CT |
| Pertac Hybrid | ESPE/Premier, Norristown, PA |
| Post Com II | Jeneric/Pentron, Wallingford, CT |
| Ultrabond | Den-Mat, Santa Maria, CA |
| Visarfil | Den-Mat, Santa Maria, CA |
| Visiomolar | ESPE/Premier, Norristown, PA |

G. Methods for Modulating the Light Source

1. Lasers

One preferred light source for use in the invention is a monochromatic laser of a wavelength matched to the dental material. Such an arrangement limits the dental material to a single initiator that absorbs light at the wavelength produced by the laser. Multiple initiators adapted for different wavelengths may be included in the dental material and multiple light sources of appropriate wavelengths for the initiators may be employed. It is preferred to use a computer-controlled laser so that the exact waveform, modulation of the wave forms and power levels of light source can be produced consistently and accurately in order to achieve the desired post-cure physical properties from the composite being cured. The computer control can control the supply of electrical current to the laser and generate a variety of frequencies in different waveforms, so that as the electrical current is increased, the power output of the laser will increase, and as the electrical current is decreased the power output of the laser will correspondingly decrease mimicking the wave form and frequency generated. A light control circuit on the output side of the laser can provide exact measurement of the laser output power and feedback to the microprocessor, thereby allowing the microprocessor to deliver the pre-programmed desired power over time.

One preferred monochromatic laser for use with a single initiator (specifically camphorquinone) dental material is a 488 nanometer laser. An argon laser can be built such that it produces a very narrow band width of light around the 488 nanometer wavelength such that all photons are utilized by the initiator. The output power is monitored and adjusted according to light source power modulation techniques described herein.

The use of a single initiator in a dental material has become the standard in dentistry. The problem with single initiator dental materials is that they limit the post-cure physical properties of the dental material. The use of multiple initiators in the dental material permits the post-cure characteristics of the dental material to be more closely tailored to the desired application and is therefore preferred. Use of multiple light sources or the ability to change wavelengths one or more times during cure is necessary in order to take advantage of the presence of multiple initiators in the dental materials. Such examples would include but not be limited to multi-wavelength lasers (i.e. Krypton Ion Argon Ion mix) and mixed combinations of different lasers (i.e. and Argon Ion laser combined with an infrared diode laser in the same housing). The wavelengths of the multi-wavelength laser can be separated utilizing filters, prisms, diffraction gratings and/or Poly Chromatic Acusto Optic Modulators (also known as Acoust-Optic Tunable Filters). The preferred method would be with the Poly Chromatic Acusto Optic Modulator because it is capable of not only separating the individual wavelengths but recombining them in any percentage desired and the device is operated by applying current directly to it rather than having an electro-mechanical interface. An appropriate Poly Chromatic Acusto Optic Modulator can be obtained from Neos Technology, Inc., 4300-C Fortune Place, Melbourne Fla. However, any of the invented methods could be controlled (in the case of the other option listed by way of electromechanical interface such as servos and solenoids) with the same computer that controls the intensity modulation. Modulation of the intensity of the various wavelengths according to the modulation schemes described herein is also advantageous.

2. Conventional Light Sources

Although the most preferred light source used in this invention is a laser, conventional light sources (light sources other than lasers) may also be used. With non-laser light sources, however, it is difficult to produce monochromatic light. As conventional light sources produce light across a broad portion of the spectrum, it is typical to use a filter to limit the light emitted to the desired wavelength. The problem is that of producing sufficient intensities of and controlling the power of the specific wavelengths needed when there is no baseline of the percentage of power that is at the needed wavelength.

As a solution to this problem, the wavelength may be optimized by modulating input current (i.e., change the frequency of the current). When a conventional filament or short arc light bulb receives a particular frequency (i.e. 60 hertz as supplied in the US) it will produce a spectrum of light that may be more intense in the red and infrared portion of the spectrum whereas if the frequency is changed or the current is pulsed the light will produce a spectrum that is more intense in the blue wavelengths. With this understanding the utility of modifying the input current of a lamp used in curing becomes clear. Applying the current frequency that produces the greatest intensity of light in the wavelength that is needed in curing process and adding filters, prisms, diffraction gratings or other wavelength separating/eliminating devices would produce the perfect curing wavelength in much greater intensity than would otherwise be possible. It is then possible to provide an excess of the desired wavelength which can then be modulated over time to produce the post-cure physical properties desired from the material.

As an example of a dental material with more than one initiator, a two initiator dental material may be used that has a first initiator active in ultraviolet light and a second initiator active in the visible blue. The primary current to the light bulb would be modulated so that the ideal frequency for maximum ultraviolet output is achieved, the appropriate filters, prisms, diffraction gratings etc. would simultaneously be integrated into the system by the computer to eliminate the unwanted wavelengths. The microprocessor would monitor the output as described herein. The current amplitude may be increased or decreased to control the output power of ultraviolet light required. At the prescribed time the frequency of the power input would be adjusted by the microprocessor to achieve the greatest output of visible blue light, simultaneously the filter or prism or diffraction grating etc. would be changed by the computer to emit only the blue light. The amplitude of visible blue light would be measured and adjusted as already described. The use of changing the current frequency combined with conventional filtering methods provides wavelength control while simultaneously increasing/decreasing the current amplitude to modulate the intensity of the desired wavelengths produce curing control previously unavailable.

H. Examples of Light Source Power Modulation

Using the general inventive concepts outlined above, tests were performed in order to evaluate various modulation scenarios and their effectiveness for curing dental materials. The tests were designed to evaluate the effect that modulating curing light intensity over time has on the physical properties of a dental restorative material. Similar results will be expected for all areas of light-activated polymerization reaction, whether the intended field is dentistry or otherwise. In the tests performed, the restorative material was Herculite XRV available from Kerr Corporation in Orange, Calif., lot number 704675, expiration date January 2000. The samples of that dental restorative material w ere prepared according to ANSI/ADA Specification Number 27 (1977). Six samples were used in each test. The samples were exposed to a particular light modulation scenario utilizing an argon laser (488 nm). The diametral tensile strength was measured in accordance with ANSI/ADA Specification 27 (1977) and the mean diametral tensile strength and standard deviation were calculated. The flexibility was assessed qualitatively and confirmed by a review of the diametral tensile strength and standard deviation. In interpreting the results, the reader should be aware that more flexible samples have a lower diametral tensile strength and the standard deviation is large due to flexing before breaking.

Test #1

Figure 7:
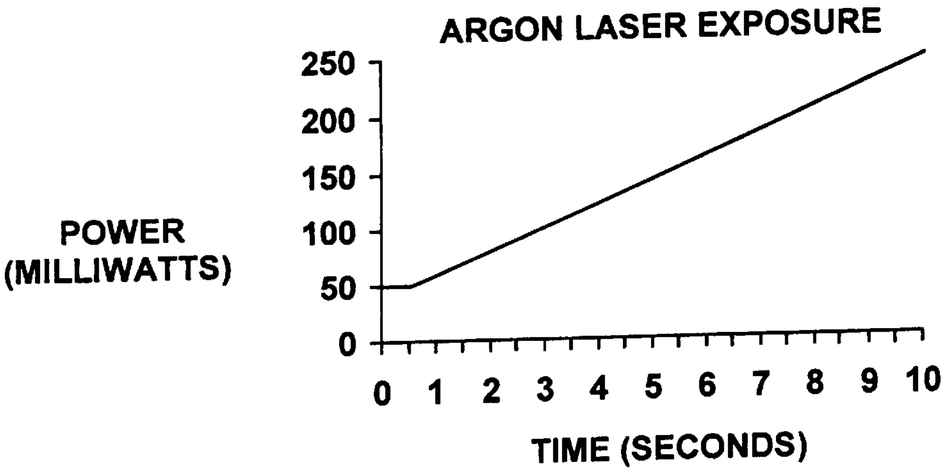
FIGS. 7–13 depict light source modulation used experimentally in the invention.

Referring to FIG. 7, it can be seen that the samples were exposed to an initially low level (50 milliwatts) of light held constant for less than a second, and the light intensity was then increased steadily over a 10 second exposure time until the curing was completed in 10 seconds at a high power level of 250 milliwatts. The results of the test were as shown in the table below. The abbreviation "Mpa" means megapascals.

| PROPERTY | RESULT |
|---|---|
| Mean Diametral Tensile Strength | 32.46 Mpa |
| Standard Deviation | 8.39 Mpa |
| Mean Diametral Shrinkage | 0.72% |

Test #2

Figure 8:
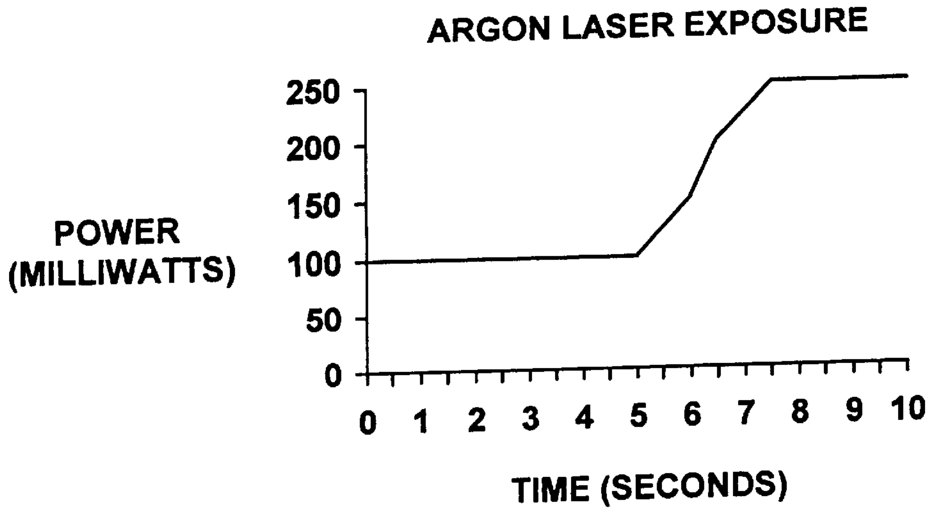

Referring to FIG. 8, it can be seen that the samples were exposed to an initially mid-level (100 milliwatts) of light held constant for five seconds, or half of the curing time. Then light intensity was increased over a 2 second period from 100 milliwatts to 250 milliwatts, and held constant at the higher power level until curing was complete. The results of the test were as shown in the table below.

| PROPERTY | RESULT |
|---|---|
| Mean Diametral Tensile Strength | 27.69 Mpa |
| Standard Deviation | 10.83 Mpa |
| Mean Diametral Shrinkage | 0.63% |

Test #3

Figure 9:
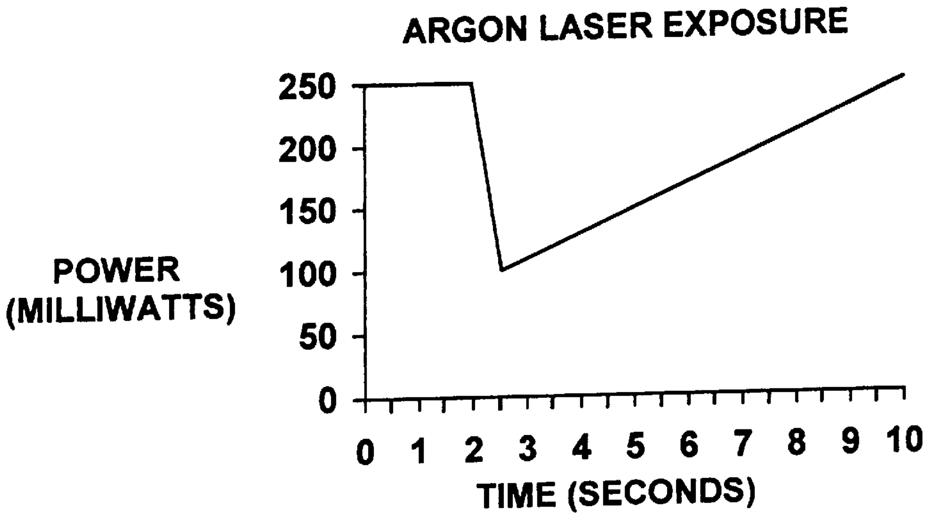

Referring to FIG. 9, it can be seen that the samples were exposed to an initially high level (250 milliwatts) of light held constant for 2 seconds. Then light intensity was abruptly decreased to a mid-level (100 milliwatts) from which it was gradually increased again to a high level (250 milliwatts) over the 10 second curing time. The results of the test were as shown in the table below.

| PROPERTY | RESULT |
|---|---|
| Mean Diametral Tensile Strength | 38.63 Mpa |
| Standard Deviation | 4.51 Mpa |
| Mean Diametral Shrinkage | 0.55% |

Test #4

Figure 10:
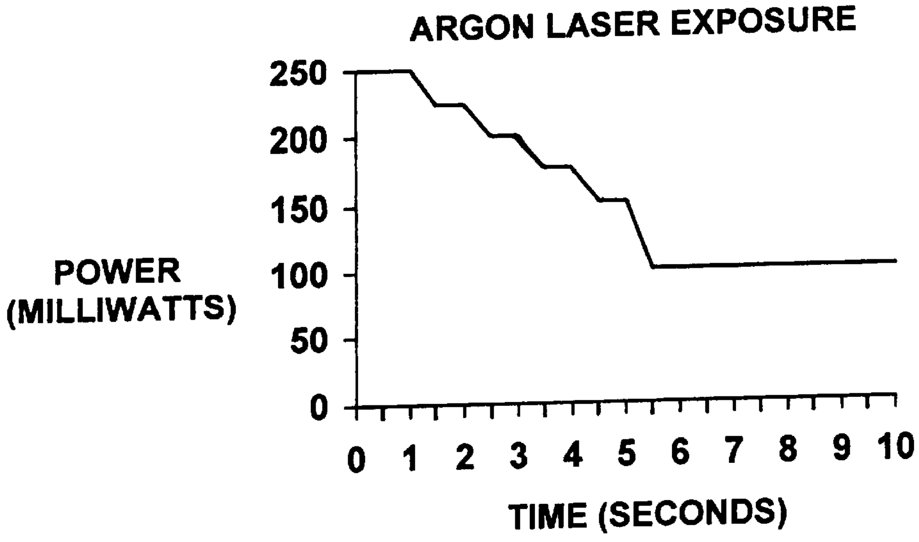

Referring to FIG. 10, it can be seen that the samples were exposed to an initially high level (250 milliwatts) of light held constant for 1 seconds. Then light intensity was incrementally stepped down about 50 milliwatts per step over 5 steps to a mid-level (100 milliwatts). At each step, the light was held constant for a brief period (about 0.5 seconds). The downward steps of light intensity were rapid but not instantaneous, as the graph shows. After 5 seconds of this gradual stepped modulation, the light level was held constant at a mid-level for the remainder of the planned curing time (in this case for an additional 5 seconds). The results of the test were as shown in the table below.

| PROPERTY | RESULT |
|---|---|
| Mean Diametral Tensile Strength | 39.55 Mpa |
| Standard Deviation | 6.47 Mpa |
| Mean Diametral Shrinkage | 0.51% |

Test #5

Figure 11:
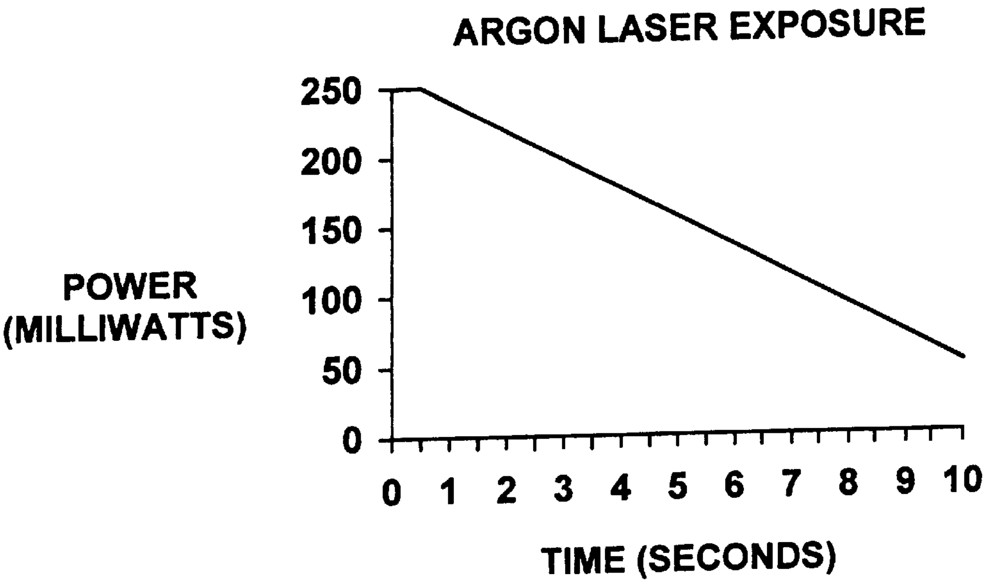

Referring to FIG. 11, it can be seen that the samples were exposed to an initially high level (250 milliwatts) of light held constant for a brief time (about 0.5 seconds). Then light intensity was gradually but continuously decreased over the remainder fo the 10 second curing time, ending at a low power level (about 50 milliwatts). The results of the test were as shown in the table below.

| PROPERTY | RESULT |
|---|---|
| Mean Diametral Tensile Strength | 34.03 Mpa |
| Standard Deviation | 5.52 Mpa |
| Mean Diametral Shrinkage | 0.49% |

Test #6

Figure 12:
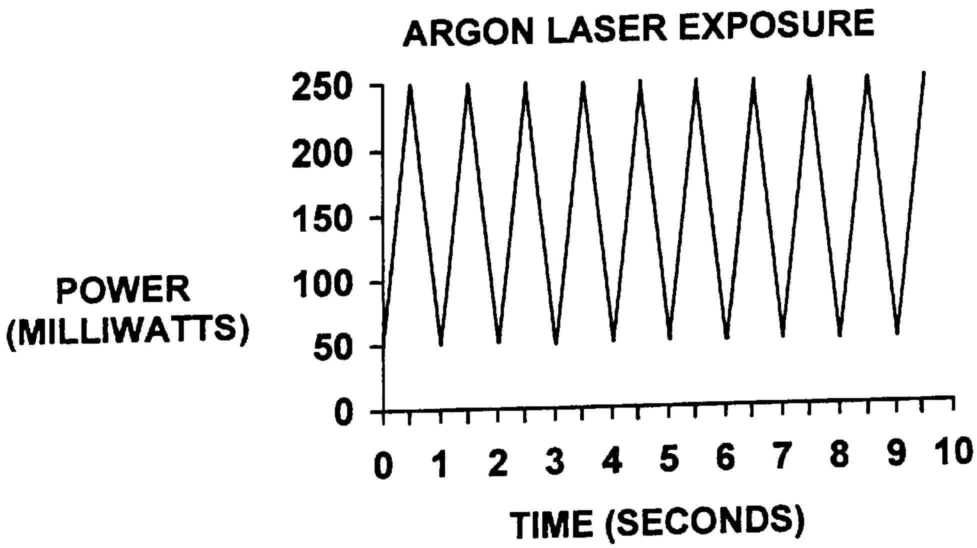

Referring to FIG. 12, it can be seen that the samples were exposed to an initial low level of light (50 milliwatts) which was rapidly increased to a high level (250 milliwatts) and decreased again to a low level (50 milliwatts) over a short time period (about 1 second). This modulation was repeated once per second over the 10 second cure time. The results of the test were as shown in the table below.

| PROPERTY | RESULT |
|---|---|
| Mean Diametral Tensile Strength | 37.37 Mpa |
| Standard Deviation | 5.20 Mpa |
| Mean Diametral Shrinkage | 0.31% |

Test #7

Figure 13:
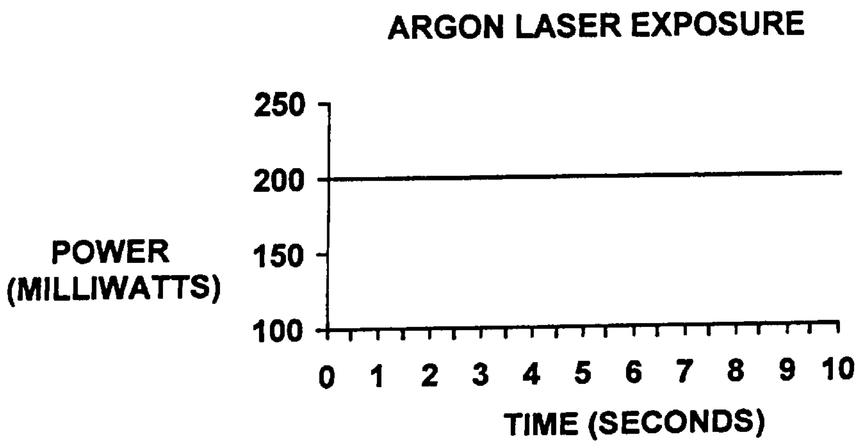

Referring to FIG. 13, it can be seen that the samples were exposed to a constant moderately high level (200 milliwatts)

of light for the entire 10 second curing time. The results of the test were as shown in the table below.

| PROPERTY | RESULT |
|---|---|
| Mean Diametral Tensile Strength | 38.80 Mpa |
| Standard Deviation | 3.68 Mpa |
| Mean Diametral Shrinkage | 0.61% |

This type of curing is the current industry standard, and the post-cure properties of the dental material are typical of those achieved in the industry without use of the invention.

Summary of Test Results

Figure 14:
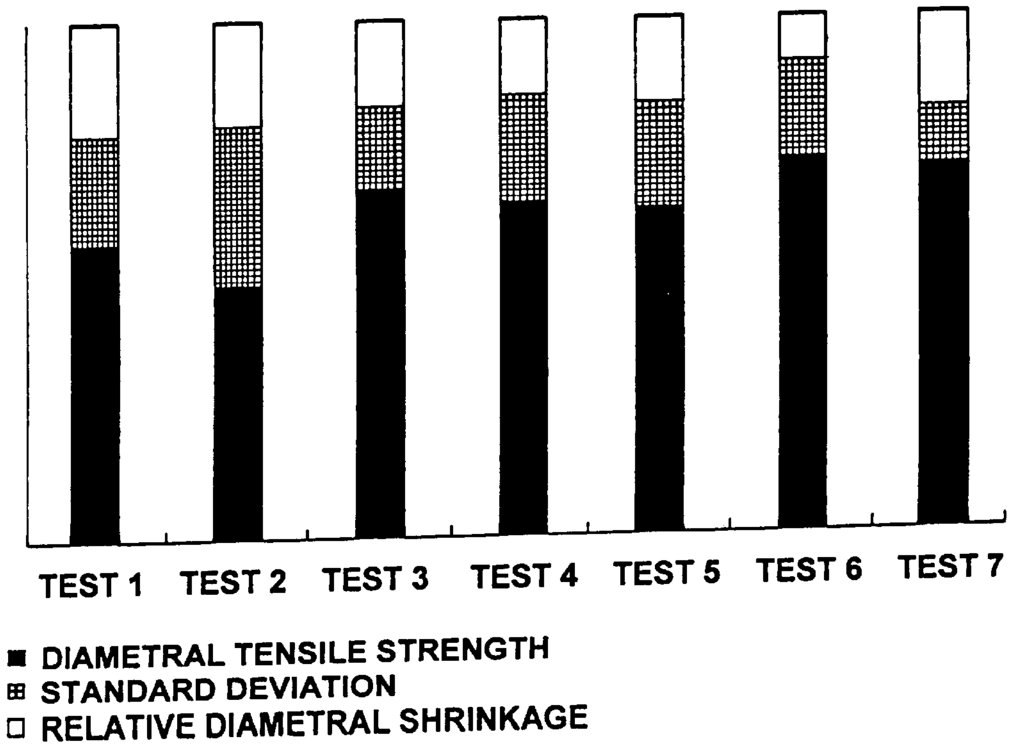
FIG. 14 depicts a graph comparing diamentral tensile strength, standard deviation and relative diametral shrinkage for the experiments performed.

Referring to FIG. 14, a graph is provided that compares diametral tensile strength, standard deviation and relative diametral shrinkage for each of the tests performed. Although for each test the same dental material was used as an input, the physical properties of cured dental materials from the different tests are significantly different from each other. Modulating the curing light power allows the physical properties of the resulting cured dental material to be designed and controlled. Additionally, the length of exposure of a dental material to a modulating light source will change its properties as well. Once the desired properties of the cured material for a particular application are known, power modulation and exposure times can be adjusted to produce a cured dental material meeting the desired criteria. By utilizing the invented modulation scenarios, the operator of a light source can easily decide which post-cure physical properties are desired for the particular dental application and then implement the modulation scheme which will achieve those post-cure properties. Alternatively, custom-cure modulation can be designed for unique applications.

I. Application to Various Dental Practice Scenarios

The scenarios below illustrate how a dental practitioner can implement the invention to achieve a superior cured dental material in his or her patients.

Scenario #1

If a dentist wishes to fill a large cavity on the occlusal (chewing) surface of a molar, the dentist would seek post-cure properties that include extreme hardness to avoid chipping on impact, flexibility to avoid the material fracturing under stress, and as little volumetric shrinkage as possible to avoid the potential for micro-leakage of bacteria into the tooth. For such an application, the practitioner would be best served by implementing the modulation scheme described for Test #4 above. A dental material cured by that modulation scheme exhibits excellent diametral tensile strength, good flexibility and only moderate shrinkage.

Scenario #2

If a dental practitioner wished to fill a small cavity at the junction where the tooth meets the gum line, he would want no shrinkage at all. Flexibility and hardness are not important in such a location because no force will be applied directly to the filling. Shrinkage, however, must be avoided so that the dentist will not need to perform any additional procedure to prevent micro-leakage. For such an application, the modulation scheme described for Text #6 above should be implemented.

Scenario #3

If a dental practitioner were applying orthodontic brackets, he or she would desire sufficient strength in the dental material to hold the brackets in place during orthodontic therapy, but it would be desirable to use a brittle dental material to permit shattering the dental material at the conclusion of orthodontic treatment without damage to the tooth or tooth enamel. At least 18 megapascals of tensile strength is needed for orthodontic applications. The practitioner should select either the modulation scheme of Test #3 or Test #7 for this application.

J. Industrial Applications

The invented modulation schemes and variations of them, while conceived of and tested for use in dentistry, have use wherever light-activated polymerization takes place. Below some examples of how the inventive concepts may be applied to other industries are listed.

INDUSTRIAL EXAMPLE #1

If an adhesive is used to bond glass and silicone to create a part for use over a broad temperature range, it is desire that the adhesive shrink to pull the glass and silicone together. But the adhesive must be flexible because glass and silicone expand and contract at different rates when exposed to heat or cold. For such an application, a polymeric composite material cured by the modulation scheme of Test #2 above is best because it provides both flexibility and shrinkage.

INDUSTRIAL EXAMPLE #2

If a filler material is needed to remove scratches and other production marks on a plastic cabinet before the cabinet is painted, the chosen filler should be as hard as possible to avoid future scratches and it should experience very little or no shrinkage in order to achieve the fastest finishing. For such an application, a polymeric composite cured by the modulation schemes of Tests #3 or #6 above depending on whether the particular application placed more emphasis on shrinkage or hardness.

INDUSTRIAL EXAMPLE #3

If a filler material is needed to restore damage to an automobile body panel, the filler should exhibit flexibility, hardness and little shrinkage. Such a balance of properties is achieved by the modulation scheme described in Test #2 above.

K. Prophetic Examples

The number of combinations of light source modulation waveforms, power levels and exposure times is infinite, and it is not possible to test more than a small subset of the possible combinations. However, a user could choose not to utilize a 10 second cure time as discussed in the tests above and instead could begin with some very short cure time and experiment with progressively longer cure times. The user could also experiment with modulating the light in intervals from a very small fraction of a second to many seconds. The user could also try mixing waveforms within a cure period. The user could utilize multiple pulses of light per second, with some or each of the multiple pulses having a different waveform.

PROPHETIC EXAMPLE #1

Figure 15:
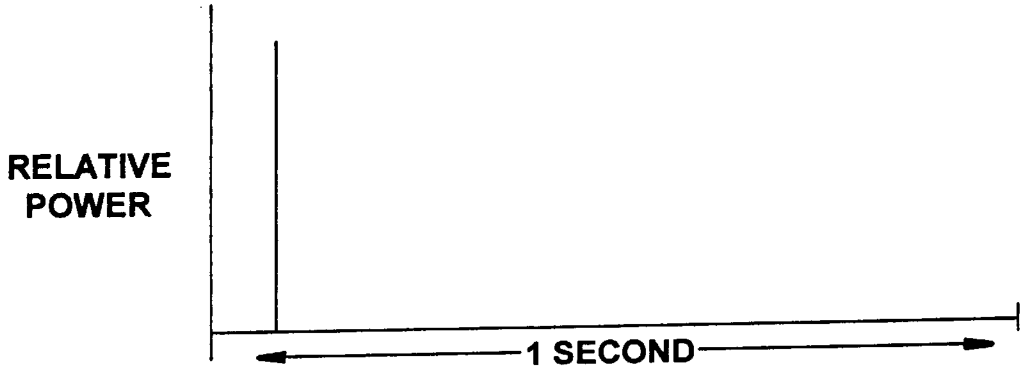
FIGS. 15–24 depict waveforms of various modulation schemes which may be used to cure a composite material.

Referring to FIG. 15, a single high intensity pulse modulation scheme is depicted. As shown, the pulse have a high level of relative power, but a very short duration, such as pico or nanoseconds.

PROPHETIC EXAMPLE #2

Figure 16:
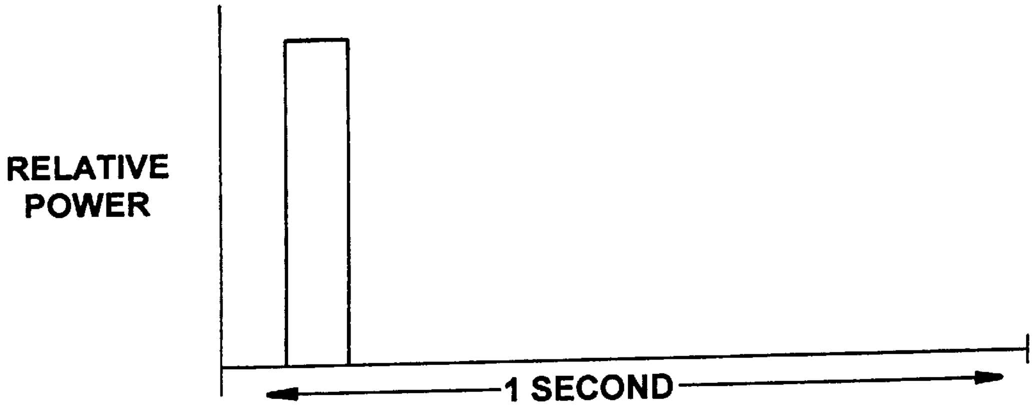

Referring to FIG. 16, a single high intensity pulse modulation scheme having a square waveform is depicted. In this example, the light source is exposed to the material to be cured at a high relative power level for a short (but not instantaneous) time period at a constant power level. The duration of the pulse can be modified to be of any desired length. Such a pulse is anticipated to be in the range of from 1 micro second or less to 0.99999+ seconds in length.

PROPHETIC EXAMPLE #3

Figure 17:
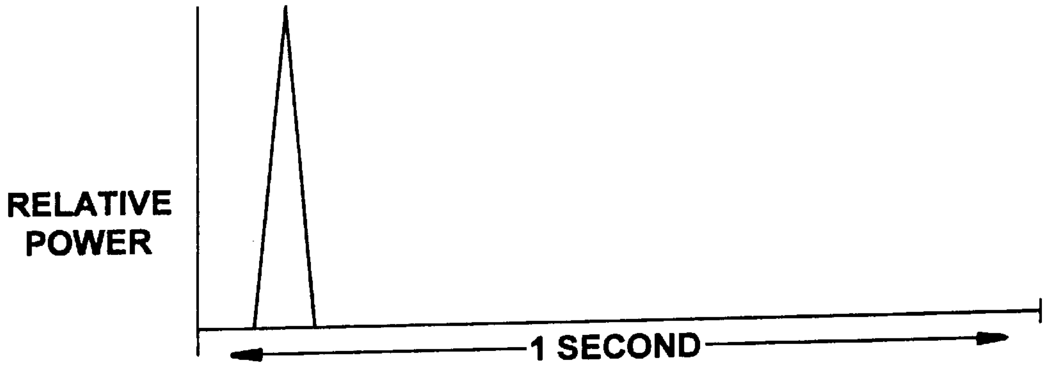

Referring to FIG. 17, a light source power modulation scheme having a triangular waveform is depicted. The duration may be modified to be shorter or longer than illustrated. The possible duration of such a waveform is from less than 1 micro second to 0.99999+ seconds in length.

PROPHETIC EXAMPLE #4

Figure 18:
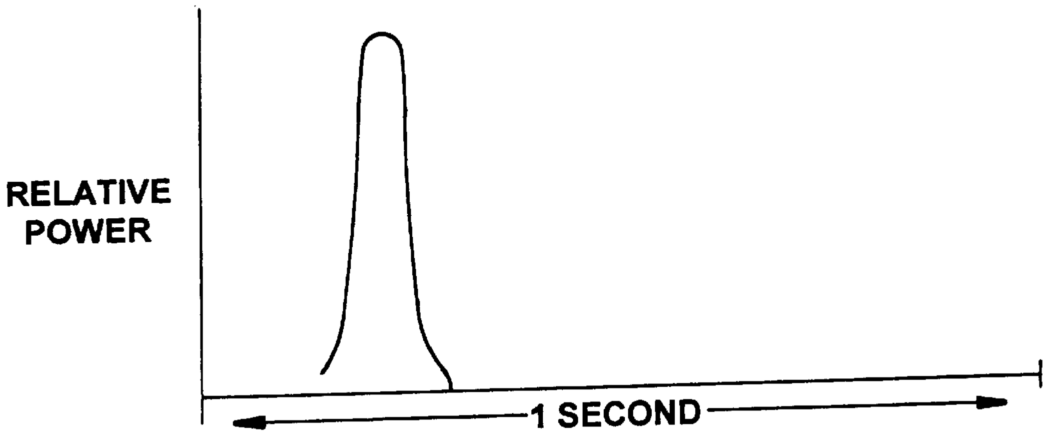

Referring to FIG. 18, a single pulse sine wave form is depicted according to which a light source for curing dental material can be modulated. The duration of a pulse of light power according to that waveform is modifiable to the desired time length, and could be from less than 1 micro second to 0.99999+ seconds in length.

PROPHETIC EXAMPLE #5

Figure 19:
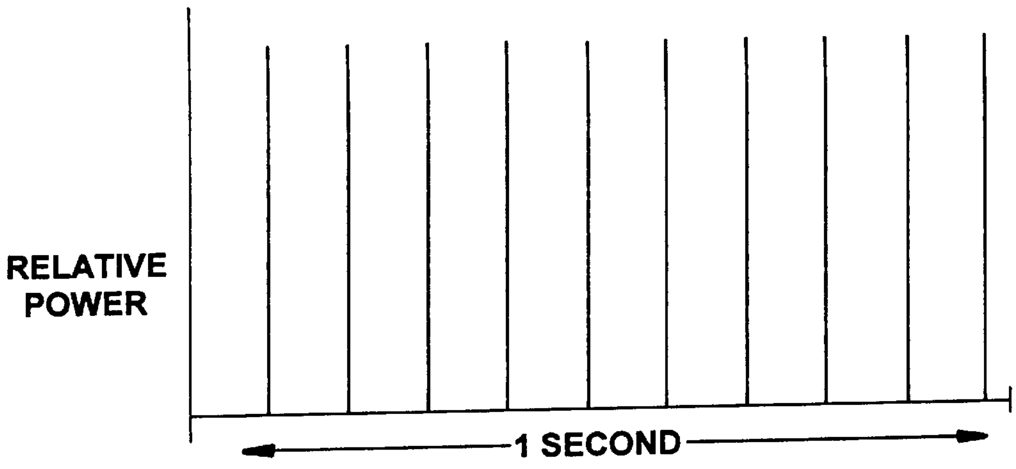

Referring to FIG. 19, a multiple pulse waveform for another modulation scheme that can be implemented according to the inventive concept is depicted. The figure depicts a single pulse of light at relatively high power in discrete intervals being repeated during a one second interval. In the figure, the pulse is repeated 10 times during a second for a frequency of 10 Hz. Of course the frequency can be adjusted from 1 Hz or less to many gigahertz or more.

L. Extremely Fast Light Modulation Test

Additional testing of light source power modulation to cure dental restorative materials was performed where the intensity of the light is turned up and down many times in less than a second and carried on through the course of the entire curing time. In this testing, the restorative material used was Herculite XRV available from Kerr Corporation in Orange, Calif., lot number 704675, expiration date January 2000. The samples were prepared using ANSI/ADA Specification Number 27 (1977) and the mean diametral tensile strength and standard deviation were calculated.

Fast Modulation Test #1

Figure 20:
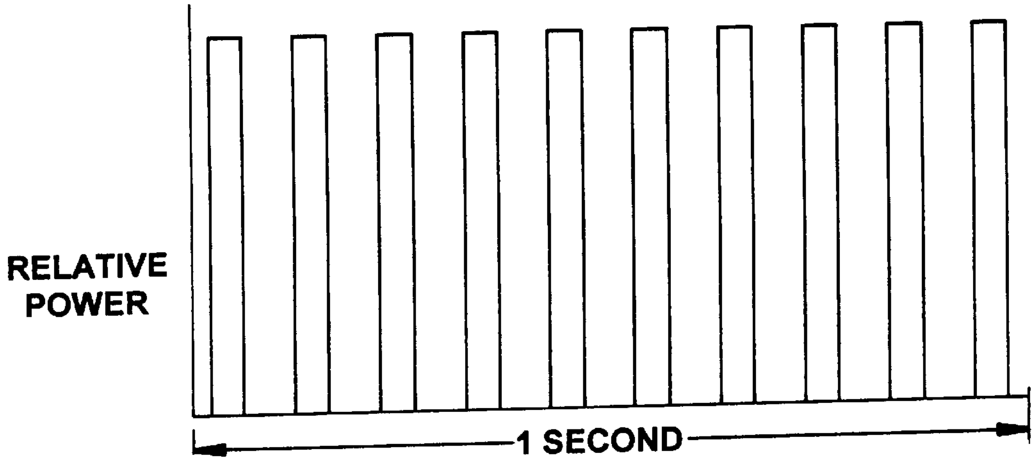

The waveform used was a square wave. The light was turned on at 250 milliwatts for 0.05 second in the square waveform, then the light was turned on for 0.05 second in a square waveform as illustrated in FIG. 20. The sequence was repeated for a total of 10 seconds The results of this test are shown in the table below.

| PROPERTY | RESULT |
|---|---|
| Mean Diametral Tensile Strength | 38.95 Mpa |
| Standard Deviation | 5.76 Mpa |

Waveform Test #2

Figure 21:
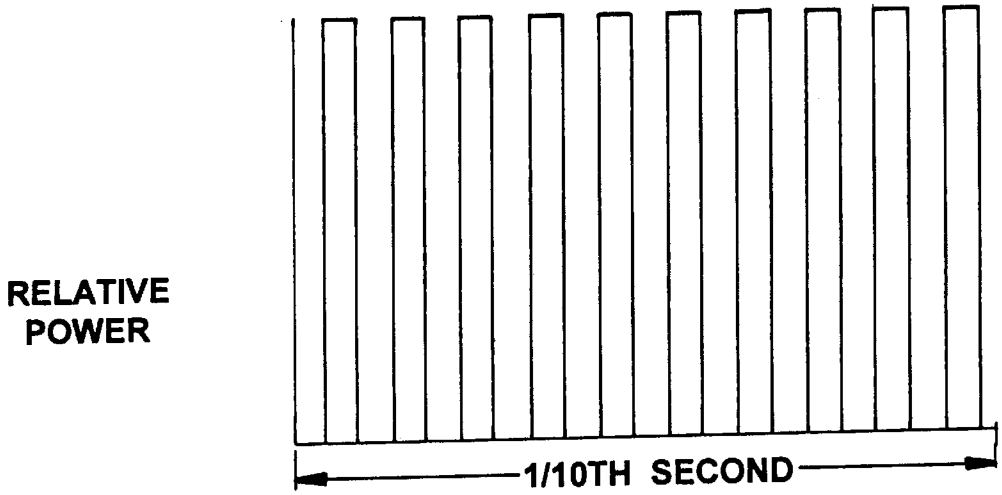

In the second test, a square waveform and 250 milliwatts of power were also used. The light was turned on for 0.005 second in the square waveform and then off for 0.005 second. The graph in FIG. 21 illustrates the waveform used. The sequence was repeated for a total of 10 seconds. The results of this test are shown in the table below.

| PROPERTY | RESULT |
|---|---|
| Mean Diametral Tensile Strength | 47.16 Mpa |
| Standard Deviation | 6.96 Mpa |

Waveform Test #3

Figure 22:
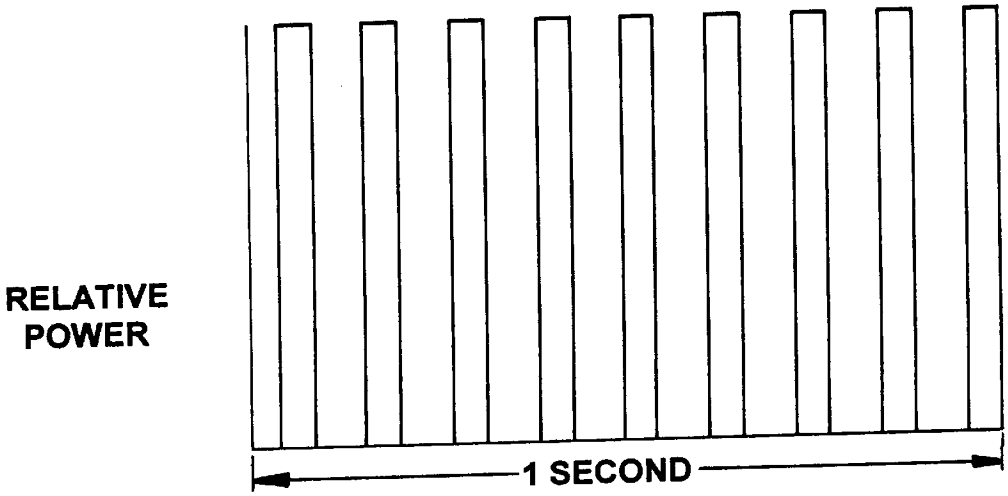

In a third test a square waveform and a 250 milliwatt power level were used. The light was turned on for 1/30th second and off for 2/30th according to the waveform illustrated in FIG. 22 (the light is off twice as long as it is on). The sequence was repeated for a total of 10 seconds. The results of this test were as shown in the table below.

| PROPERTY | RESULT |
|---|---|
| Mean Diametral Tensile Strength | 34.94 Mpa |
| Standard Deviation | 7.47 Mpa |

Waveform Test #4

Figure 23:
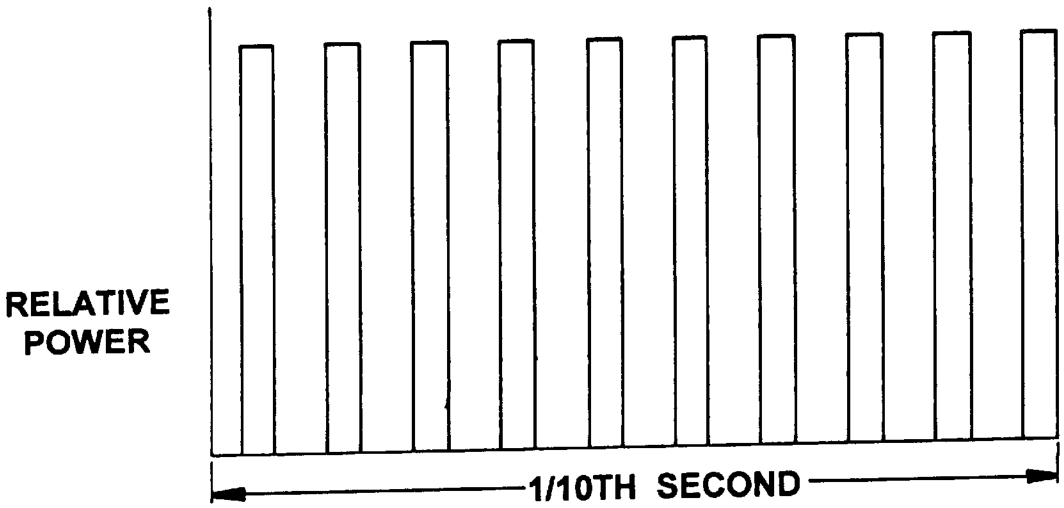

In the fourth test, a square wave form according to FIG. 23 was used with a 250 milliwatt power level. The light was turned on for 1/300th second and then turned off for 2/300th according to the waveform illustrated in FIG. 23 (the light is off twice as long as it is on). The sequence was repeated for a total of 10 seconds. The results are shown in the table below.

| PROPERTY | RESULT |
|---|---|
| Mean Diametral Tensile Strength | 40.09 Mpa |
| Standard Deviation | 3.16 Mpa |

When the results of these studies are compared, it is clear that modulating the light extremely fast (many times per second) has a profound effect on the post-cure physical properties of the material. For example, with a square wave form and 250 milliwatts of power for the same time interval, turning the light on and then off 100 times per second (on for $1/200^{th}$ and off for $1/200^{th}$) yielded a diameteral tensile strength of 47.16 Mpa but when the light was turned on and off only 10 times per second (on for $1/20^{th}$ and off for $1/20^{th}$) the diametral tensile strength was 38.95 MPa, with the difference being statistically significant. In both sets of samples the intensity of the light was 250 milliwatts, in both sets of samples the light was on for a total of 5 seconds and off for a total of 5 seconds and yet there post-cure properties were very different. The only difference between the exposure of the 2 sets is that in one set the light was turn on and off at a rate that was 10 times faster than the other.

The only difference between the first two tests and the second two tests is that the light was turned off for twice as long as it was turned on, that is to say that the light was turned on for $1/300^{th}$ of a second and then turned off for $2/300^{th}$ of a second. When considering the results of the second test, the difference in tensile strength was 40.09 MPa compared with 34.94 MPa, which approaches statistical significance. It is interesting that the samples that were turned on and off 100 times per second attained greater strength than the industry standard constant power exposure (38.8 MPa), suggesting that a beneficial result can be obtained by rest periods (periods without exposure to light) during the cure cycle. Also comparing the 10 times on and 10 times off sample to the industry standard constant power exposure, it can be seen that the 10 times on and 10 times off sample attained similar tensile strength with only 1/3 of the light exposure time. In other words the total exposure time (light on) was 3.33 seconds whereas in the industry standard the light remains on for the entire 10 seconds.

Because in the last test the light was only on for a total of 3.33 seconds and the extent of polymerization was at least as good as the current industry standard the test suggest in no small way that very discreet changes in power intensity over the course of the cure can have dramatic effects on the post-cure physical properties.

M. Summary

Figure 24:
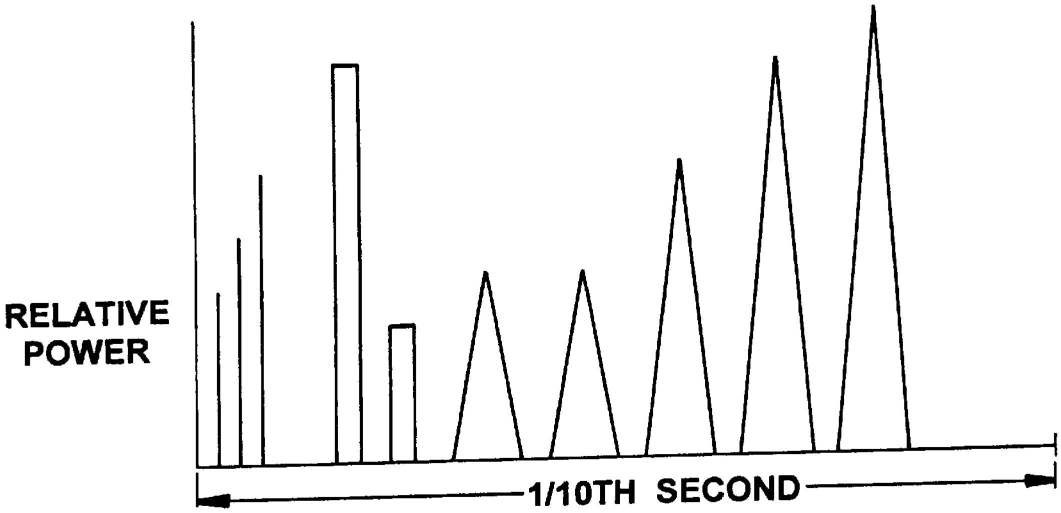

When one combines different wave forms with variable pulse widths and variable on/off rates, the possible permutations are infinite. For example, one could generate a pattern of 3 pulses, 2 square waves of 1 micro second duration and a single sine wave of 5 micro seconds duration then repeat the scenario 10 times per second. One could further modify the scenario by increasing and decreasing the power of the light source between each pulse or wave. FIG. 24 depicts an example of this type of modulation. In FIG. 24, the first of the three pulses begins at a lower relative power level and increases with each pulse. After a time without light output of any kind (a rest period), a square wave of much higher relative power is generated with a predetermined pulse width. Following the first square wave is a second square wave of lower relative power with the same pulse width. Another rest period is implemented followed by 4 triangular waves, each followed by a rest period, the first 2 being equal in magnitude and each of the succeeding 2 being of greater magnitude than its predecessor. This series could be repeated many times during cure of a material, or it could be preceded or followed by other modulation. Wave forms may be intermixed and vary in pulse width. The rest periods can be increased, decreased, placed in a different location in the series or omitted. This example is provided to illuminate possible complexity of the modulation scheme within the invention that a user may implement, anything from on single high or low intensity pulse to an infinitely complex modulation that goes on for minutes in a material that contains several initiators that require different wavelengths.

N. Equipment Discussion

Figure 25:
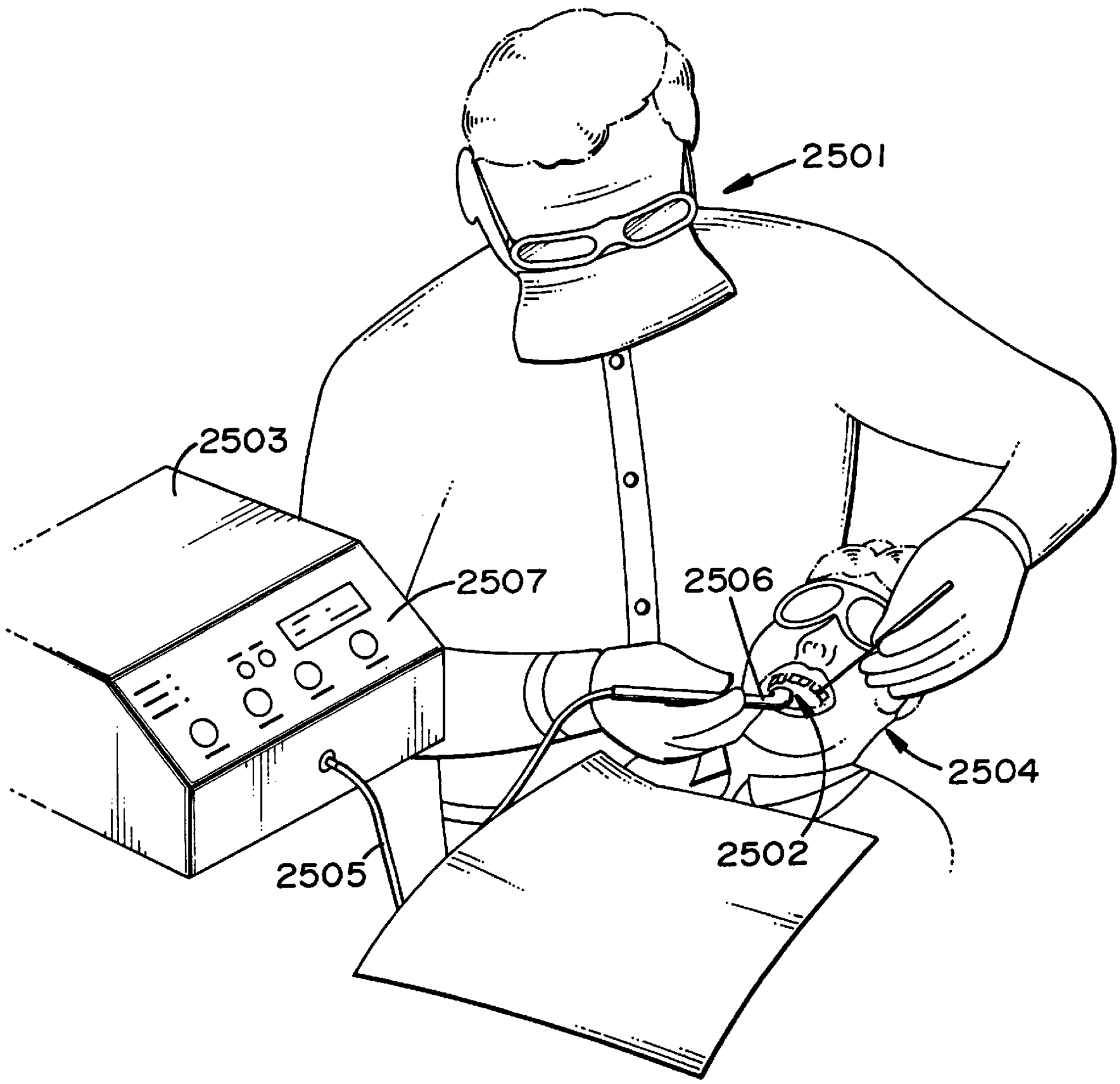
FIG. 25 depicts a dentist using the invented method to cure composite material in a patient's mouth.

Referring now to FIG. 25, a representation of the invention being employed in one particular environment is provided. The figure depicts a dental office with the light source at chairside. The dentist 2501 applies the curing light 2502 that is produced by a light source 2503 to the patient 2504 by way of a light conducting device 2505 and a light delivery device 2506. The apparatus used to deliver light to the patient 2504 includes two basics parts: a fiber optic or fluid filled wave guide 2505 which is attached to the light generating source 2503 and conducts that light to the delivery handpiece 2506. The delivery handpiece 2506 preferably would have a fiber anchor system to hold the fiber securely in the handpiece, and mirrors, prisms, lens, windows or other structures to manipulate the light such that it can be delivered to the teeth in the desired manner. In this configuration, the light source 2503 within its interior includes either hardware circuitry to perform the desired modulation or a microprocessor running software that performs the desired modulation. Inputs could be accepted from a control panel on the light source 2503 in order to permit the user to select or vary the modulation scheme.

In its simplest configuration, hardware of the invention would simply incorporate an electronic circuit that would run a predetermined modulation program in a conventional dental curing light. Such a device could be shaped like a pistol, could have a rechargeable battery pack or a power cord that would plug directly into a wall outlet, could have a simple electronic circuit that turns the light up and down to predetermined intensities at a predetermined rate, could use a conventional light source, could have a narrow pass filter allowing only the desired curing wavelengths to pass and could have a glass rod that the filtered light is directed into and subsequently conducts that light to the tooth. The dentist need only plug it in, point it at the tooth and pull the trigger (i.e. push the button) that engages the automatic modulation program.

In a slightly more complex yet relatively simple configuration the invention could be rearranged such that the device and its control panel deliver electrical current rather than light to a set of electrical conductors. The conductors would then deliver the electrical current to a light source, conventional or laser, that is housed in the handpiece. In such a configuration the filters, prisms, diffraction gratings, frequency multiplying crystals, Poly Chromatic Acusto Optic Modulator or any other wavelength separating, mixing or eliminating device could be incorporated into the handpiece housing after the light source for light generation and control.

Another gross configuration of the invention would have the device that produces the light 2503 placed in a remote location in order to save space and money. In this configuration there could be several light conducting devices 2505 attached to the light producing device 2503. These light conducting devices would be long enough to go from the remote location to the dental chair where the light would be needed. With several of them attached a dentist could have a light conductor 2505, a handpiece 2506 and a control panel 2507 at each dental chair in the office. By incorporating mirrors and electo-mechanical interfaces between the actual light source and light conductor the dentist could make the appropriate command at the control panel and the light would be focused into the light conductor going to the chair where the light is needed. In this way the dentist would only need one light producing device, one central processing unit (computer control) and one set of wavelength separating/eliminating devices described herein which are the most expensive and space consuming items in the invention. They are also the most complex feature used and invention and the interaction between them is an important concept to the invention.

Figure 26:
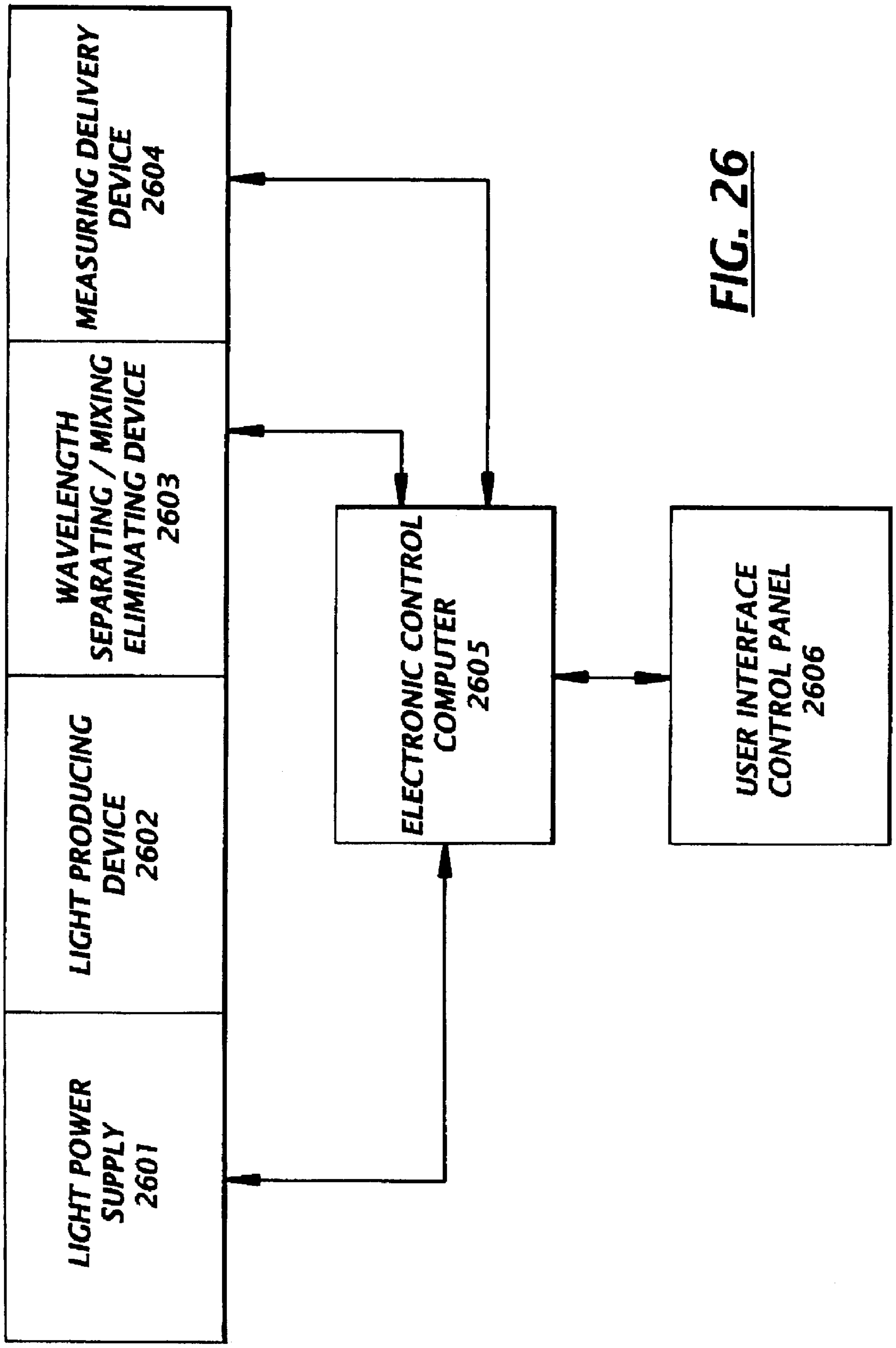
FIG. 26 depicts a block diagram of a system which can be used to carry out the invention.

A component description and some interactions between them is illustrated in FIG. 26. The Light Power Supply 2601 is an electronic device that accepts power from an outside source (an electrical outlet in the dental office) and converts it into a voltage and current that can be utilized by the Light Producing Device 2602. The power supply 2601 can be as simple as a current controlling device such as a potentiometer which is simply turned up and down to increase and decrease the current and subsequently the intensity of the light being produced by the Light Producing Device 2602, or it can be extremely complicated containing current storage devices such as capacitors, frequency generators, fast switching circuits and other electronic and electrical devices that would drive the Light Producing Device 2602 to produce very rapid modulation up to tens of thousands or millions of times per second where the modulation also includes various different and complex waveforms as described herein. This complicated power supply 2601 could also simultaneously supply current of the correct frequency to maximize the production of the desired wavelength from conventional light producing devices. The Light Power Supply 2601 is controlled by interfacing with the Electronic Control 2605 (typically a microprocessor running appropriate software that implements the modulation scheme being used).

The Light Producing Device 2602 is the source for the unprocessed light. It can include a conventional light bulb such as a filament light bulb or special bulbs such as quartz halogen bulbs or bulbs filled with exotic gasses such as neon and argon or lamps such as short arc lamps and lamps filled with special gasses such as mercury vapor or sodium vapor. The Light Producing Device 2602 can included lasers such as Ion lasers, solid state lasers, diode lasers, crystal lasers, dye lasers and eximer lasers. The Light Producing Device 2602 could contain a mixture of any or all of the potential lights sources available. For instance it could include a infrared diode laser the wavelength from which could be used directly to cure the composite and then diverted to pump or excite a crystal laser the wavelength from which would then be used to further cure the initial composite or could be used to cure a different composite. An Ion laser such as argon ion and a lamp such as a mercury vapor lamp could also be incorporated into the example. In this example the configuration would include three lasers and a lamp all of which are 'driven' or powered by the Light Power Supply 2601 which is controlled by the Electronic Control 2605.

The Wavelength Separating/Mixing/Eliminating Device 2603 receives the light from the Light Producing Device 2602 and manipulates the varies wavelengths that it receives. The device can be a simple as one narrow pass filter but may be very complex consisting of filters, prisms, diffraction gratings, frequency multiplying crystals and Poly Chromatic Acusto Optic Modulators, acusto optic tunable filters and the appropriate optical (lens, mirrors etc.) electro mechanical interfaces (servos, solenoids etc.) to manipulate them. An example would be that the Light Producing Device 2602 contains an infrared diode laser that emits 810 nm, a crystal laser that produces 1064 nm when pumped with the 810 nm diode laser, an argon ion laser which produces 488 nm and a mercury vapor lamp that produces (when applied with the correct frequency) excess light in the ultraviolet region. A composite contains 4 initiators: one that absorbs at 405 nm, one that absorbs at 1064 nm, one that absorbs at 488 nm, and one that absorbs at 310 nm. The composite requires a specific modulation of 405 nm for 3 seconds followed by a specific modulation of 488 nm for 5 seconds followed by a specific modulation of 1064 nm for 1 second followed by a specific modulation of 310 nm for 7 seconds and then a specific mixture of wavelengths comprised of 35 percent 488 nm, 25% 405 nm and 40% 310 nm for 4 seconds. To cure the composite the user selects the specific program and initiates the cure cycle using the user interface or control panel 2606. The Electronic Control 2605 interfaces with the Light Power Supply 2601 which fires the 810 nm diode laser and simultaneously the Electronic Control 2605 interfaces with the Wavelength Separating/Mixing/Eliminating Device 260 causing two solenoids to rotate bringing two mirrors into alignment. The first mirror directs the 810 nm beam through a frequency doubling crystal which converts the 810 nm wavelength into 405 nm, the second mirror directs the newly created 405 nm beam into the Poly Chromatic Acusto Optic Modulator which allows the beam to pass directly into the Measuring Delivery Device 2604 (and subsequently out to the composite). After the full 3 second exposure the Electronic Control 2605 turns off the 810 nm diode laser and returns the mirrors to their original position then fires the argon laser which emits 488 nm. This beam fires directly into the Poly Chromatic Acusto Optic Modulator which allows the beam pass directly to the Measuring Delivery Device 2604 (and subsequently out to the composite). After the full 5 second exposure the Electronic Control 2605 turns off the argon ion laser and fires the 810 nm diode laser simultaneously the Electronic Control 2605 interfaces with the Wavelength Separating/Mixing/Eliminating Device 2604 causing mirrors to direct the 810 nm beam into the Nd:YAG crystal laser which produces a 1064 nm beam which fires directly into the Poly Chromatic Acusto Optic Modulator which allows the beam to pass directly to the Measuring Delivery Device 2604 (and subsequently out to the composite). After the full 1 second exposure the Electronic Control 2605 turns off the 810 nm diode lasers and returns the mirrors to their original position then fires the mercury vapor lamp the light from which is focused through a lens onto a diffraction grating. Simultaneously the Electronic Control 2605 interfaces first with the Light Power Supply 2601 instructing it to produce and send a current frequency that is ideal for ultra violet light production to the mercury vapor lamp and then with the Wavelength Separating/Mixing/Eliminating Device 2603 which rotates a solenoid attached to the diffraction grating. The diffraction grating has separated all of the wavelengths produced by the mercury vapor lamp into a 'rainbow' band of wavelengths. The solenoid rotates the diffraction grating so that that portion of the rainbow that is rich in 310 nm wavelengths is directed into a narrow pass filter that eliminates all wavelengths except 310 nm the wavelengths then pass into a series of lens that psuedo collimate the wavelengths. The 'collimated' light is then directed to the Poly Chromatic Acusto Optic Modulator which directly passes the light to the Measuring Delivery Device 2604 (and subsequently out to the composite). After the full 7 second exposure the Electronic Control 2605 shuts off the mercury vapor lamp and returns the diffraction grating to its original position. The Electronic Control 2605 then interfaces with the Light Power Supply 2601 and turns on the 810 nm diode laser, the argon ion laser, and the mercury vapor lamp enclosed in the Light Producing Device 2602 and it simultaneously interfaces with the Wavelength/Separating/Mixing/Eliminating Device 2603 directing it to produce 488 nm, 405 nm and 310 nm wavelengths as described above. All three of these wavelengths are passed into the Poly Chromatic Acusto Optic Modulator which receive directions from the Electronic Control 2605 to mix the relative intensity of the various wavelengths to 35% 488 nm, 25% 405 nm and 40% 310 nm. The mixture is then modulated according to the need for the prescribe remaining 4 seconds. The Electronic Control 2605 then turns off all light sources and returns all mirrors and diffraction gratings to their original position. The Poly Chromatic Acusto Modulator can not only mix a variety of wavelengths but it can also modulate different wavelengths in different modulation patterns simultaneously. When a sophisticated Light Power Supply 2601 is combined with a sophisticated Electronic Control 2605 and a Poly Chromatic Acusto Optic Modulator extremely complicated modulation patterns which includes many wavelengths simultaneously can be produced for curing composites.

The Measuring Delivery System 2604 can also incorporate a wavelength converting or eliminating feature, particularly in the delivery portion of the system. For instance the glass fiber or waveguide can directly affect the wavelengths either by being doped with material that absorbs the incident wavelength and fluoresces a new wavelength or the glass itself can be a colored fiber that filters out unwanted wavelengths or a waveguide can be used to directly filter unwanted wavelengths. An example of a doped glass fiber would be a scenario which includes a fiber made of Zblan fluoride glass that is doped with 0.5% erbium and 5.55% yttrium. When this glass fiber is struck by 980 nanometer light (a common wavelength in infrared diode lasers) it absorbs the light and produces visible blue light centered around 465 nanometers. Camphorquinone is and initiator which absorbs light preferentially, centered at 465 nanometers. Glass fibers that are doped with various fluorescing material or custom doped glass fibers are commercially available from Galileo Electro-Optics Corporation of Strubridge Mass.

An example of a glass fiber that works as a filter would be common silica glass that has specific dyes incorporated in it just as filters do. In this scenario the fiber delivery system becomes the filter as well. Fibers of this type can be custom built by Galileo Electro-Optics Corporation of Strubridge, Mass. or are commercially available from fiber optic companies such as Fiber Optic Technology, Inc. of Pomfret, Conn.

A waveguide example would be a fluid filled waveguide. Commercially available from Oriel Liquid Light Guides of Stratford, Conn. these fluid filled waveguides are very versatile in that depending on what fluid is used they only allow certain wavelengths to pass, absorbing the remaining light. For instance one might have a fluid such as water that absorbs infrared but passes or conducts most of the visible spectrum. Such a fiber would remove all of the 'heat' generated from a short arc lamp while allowing the remaining spectrum to pass through.

The Measuring Delivery System 2604 can be as simple as a coupling mechanism for the delivery system such as a coupling for a glass fiber or fluid filled light guide. Or it can be complicated comprising beam splitters which split off a small amount of the light, photo diodes which measure that small amount of light and send a signal back to the Electronic Control 2605, shutters which open and close to stop or permit light to enter the 'fiber', mirrors, optics (lens) and electromechanical devices utilized when the entire device is located in a remote location to direct the light to different 'fibers' that end up at different dental chairs.

The intent of the Measuring Delivery System 2604 is to first, in its simplest form, to provide a connection point for the light delivery system (i.e. glass fiber optic, fluid filled wave guide, glass rod etc.) and secondly to measure the light coming out of the source and communicate that information to the Electronic Control 2605. The Electronic Control 2605 then interprets the information and makes appropriate adjustments to the Light Power Supply 2601 and/or the Wavelength Separating/Mixing/Eliminating Device 2603.

The Electronic Control 2605 could be as simple as current adjustment device such as a potentiometer that is directly integrated into the Light Power Supply 2601. In this simple scenario the operator would manually turn the potentiometer up and down to predetermined intensities at a predetermined rate. Another simple configuration would be an unsophisticated electronic circuit which would automatically increase the current and/or frequency of the current automatically once initiated by the user (i.e. the user pushes a button). The Electronic Control 2605 can be extremely sophisticated having multiple interfaces to the Light Power Supply 2601, the Wavelength Separating/Mixing/Eliminating device 2603, the Measuring Delivery Device 2604 and the User Interface 2605 and incorporating very fast multi-tasking microprocessors enabling it to control all functions of the device.

The User Interface 2606 can be a simple as a button or foot switch that is engaged by the operator and as sophisticated as a computer that interfaces with the Electronic Control. In the invention's most sophisticated form the User Interface would consist of a computer key board and a computer display (i.e. CRT or LCD) and the Electronic Control would be a sophisticated computer.

A. Sample Software

Below some computer source code is listed which implements some of the methods of the invention. This code is considered illustrative and not in any way limiting of the scope of the invention. Persons implementing the inventive concepts could use similar or different code, instructions programmed into ROM (read only memory), a custom semiconductor chip, hard-wired circuitry, manual modulation adjustment or other techniques for carrying out the invention.

The software implements a modulation scheme by traversing a table of steps. Each step describes the power level and the duration at that level. There is a diagnostic messaging system that will give indication of the current state of the profiler test state machine. There is also a command handler that allows for dynamically setting values into the current profile for testing. The normal use is to program several profiles into the ROM and select the desired profile from the front panel menu. The execution of the selected profile is accomplished by copying the profile from ROM into RAM and then executing. This allows temporary minor changes to any ROM profile for testing.

The following is a description of the commands that are used to dynamically setup a profile in RAM for testing purposes. The ANAME@ command is used to identify the profile. The ASTEP@ command accepts three arguments: The step number, the power level, and the duration in milliseconds. The AREAD@ command will display the current profile settings.

```
const CMD cmd_table[ ] = {
    {"NAME",    4, CMD_name    },
    {"READ",    4, CMD_read    },
    {"STEP",    4, CMD_step    }
};
```

The following is the profile structure used in the software. Each profile consists of several steps each of which contain a mode selection (step/ramp [1]) a power level and a time value. The laser output is adjusted to the current power and either maintained at that level or ramped to the next step power level.

```
/*{
XXXXXXXXXXXXXXXXXXXXXXXXXXXXXXXXXXXXXXXXXXXXXXXXXX
XXXXXXXXXXXXXXXXXXXX */
/* FILE : profile.h              */
/*
************************************************************************
*/
#define MAX_STEPS 20
```

-continued

```
#define MAX_PROFILES 6
typedef struct tagProfileStep
{
char mode;
int time;
int power;
}sProfileStep;
typedef struct tagProfile
{
int timer;
char index;                  /* current step index */
char name[17];               /* name of profile */
sProfileStep step[MAX_STEPS];     /* steps in profile */
}sProfile;
extern void setupProfiler(void);
extern void copyProfile(char idx);
/*}
XXXXXXXXXXXXXXXXXXXXXXXXXXXXXXXXXXXXXXXXXXXXXXXXXXX
XXXXXXXXXXXXXXXXXXXXXXX */
```

The following code section is a test routine selected via the front panel menu. The test mode is implemented as a state machine that will setup and execute a given profile. The profile is selected via the menu sub system and execution starts when the foot switch is activated. Diagnostic messaging will report the current state of the state machine via the serial communications port.

```
case TEST_MODE:
  {
  if ((HardwareStatus & keystatus) == 0)          /* IP key is OFF */
    {
    reset = 1;
    ExecutiveState = STARTUP;
    break;
  }
  switch (testState)
  {
  case SETUP:
    {
    putch_com('S');                     /* SETUP */
    ProfileRAM.index = 0;               /* Initialize the index */
    operate_shutter(OPEN);          /* Allow the shutter to open */
    testState = WAITING;                /* Goto next state */
    putch_com('W');                     /* WAITING */
  }
  case WAITING:
  {
    if ((HardwareStatus & footstatus) != 0) /* If foot switch is pressed */
      {
      putch_com('R');             /* RUNNING */
      powerTime = ProfileRAM.step[ProfileRAM.index].time;
      OPERATEON              /* Turn on the OPERATE light */
      adjust_power(ProfileRAM.step[ProfileRAM.index].power, ABSOLUTE);
      SysStat |= calflag;            /* Disable calibration */
      testState = RUNNING;              /* Goto RUN MODE */
    }
    else           /* Wait for foot switch to be pressed */
    {
      HandleModeSwitches(ROVING); /* allow free roaming of displays */
      HandleDisplay(Display);          /* Update Display */
      if (Display != TESTMODE)      /* If menu changed goto Main mode */
    {
    ExcecutiveState = MAIN_OP_MODE;
    }
  }
  break;
}
case RUNNING:
{
  if ((HardwareStatus & footstatus) != 0) /* If foot switch is pressed */
    {
    HandleDisplay(Display);
    if (Display != TESTMODE)
    {
    ExecutiveState = MAIN_OP_MODE;
    }
    if (powerTime == 0)
```

-continued

```
    {
      ProfileRAM.index ++;
      if ((ProfileRAM.index >= MAX_STEPS)||
        (ProfileRAM.step[ProfileRAM.index].time < 0))
      {
      ProfileRAM.index = 0;
      testState = PROFILEDONE;
      BUZZCOUNT(2)        /* Beep to indicate profile done */
      putch_com('D'); /* DONE */
      }
    powerTime ProfileRAM.step[ProfileRAM.index].time;
    adjust_power(ProfileRAM.step[ProfileRAM.index].power, ABSOLUTE);
      }
  }
  else              /* Abnormal termination of the sequence! */
  {
    clearBeeper();            /* Reset the Beep Timer */
    BUZZCOUNT(3)              /* Beep to indicate terminated early */
    testState = PROFILEDONE;        /* Goto DONE */
    putch_com('E');         /* ERROR */
    }
    break;
}
case PROFILEDONE:
{
  SysStat &= ~calflag;      /* Re-enable calibration */
  HandleDisplay(Display);      /* Display the currently selected */
  HandleModeSwitches(ROVING);    /* allow free roaming of displays */
  OPERATEOFF              /* Turn off the OPERATE light */
  adjust_power(25, SET);         /* Adjust power to minimum */
  SysStat &= ~beepLong;
  if ((HardwareStatus & footstatus) == 0) /* Wait for foot release */
    {
    testState = SETUP;
    }
    break;
    }
    default:
    {
    testState = SETUP;
    }
  }
  break;
}
```

While complexity for its own sake is not an object of the invention, the foregoing material illustrates the ability of persons utilizing the inventive concept to tailor their modulation scheme in order to create post-cure materials having specific desired physical properties, and that the invention can be utilized for very sophisticated applications.

The foregoing provide only a few examples of the many modulation schemes, power levels, light sources, frequencies, polymeric materials and curing times that could be applied using the inventive concepts. Further, only a few fields where the inventive concepts could be applied have been listed.

While the present invention has been described and illustrated in conjunction with a number of specific embodiments, those skilled in the art will appreciate that variations and modifications may be made without departing from the principles of the invention as herein illustrated, as described and claimed. The present invention may be embodied in other specific forms without departing from its spirit or essential characteristics. The described embodiments are considered in all respects to be illustrative and not restrictive. The scope of the invention is, therefore, indicated by the appended claims, rather than by the foregoing description. All changes which come within the meaning and range of equivalence of the claims are to be embraced within their scope.

We claim:

1. A method for obtaining a cured a polymeric dental material comprising the steps of:

(a) preparing the dental material for application to a dental surface, said dental material including monomers and at least one initiator, the initiator being sensitive to light of a particular wavelength, (b) applying the dental material to a dental surface, (c) accessing a light source capable of producing light of the wavelength that the initiator is sensitive to, (d) exposing the dental material to light from said light source at a first power level, said light including light of the wavelength to which the initiator is sensitive, thereby causing the initiator to initiate polymerization of at least some of the monomers in the dental material into polymers, (e) simultaneously decreasing the power level of said light to a second power level that is lower than said first power level while simultaneously continuing to expose the dental material to the light, (f) maintaining said light at about said second power level and continuing to expose the dental material to said light until the dental material is substantially polymerized.

2. A method as recited in claim 1 wherein said first power level is about 250 milliwatts.

3. A method as recited in claim 1 wherein said second power level is about 100 milliwatts.

4. A method as recited in claim 1 wherein said second power level less than about half of said first power level.

5. A method for obtaining a cured a dental composite comprising the steps of:

(a) obtaining a dental material which contains an initiator sensitive to light of a particular wavelength, (b) accessing a light source capable of producing light of the wavelength that the initiator is sensitive to, (c) exposing the dental material to light from said light source at a first power level, said light including light of the wavelength to which the initiator is sensitive, thereby causing the initiator to initiate polymerization of at least some of the dental material, and (d) simultaneously increasing the power level of said light to a second power level that is greater than said first power level while simultaneously continuing to expose the dental material to the light.

6. A method as recited in claim 5 wherein exposing the dental material in step (c) is performed for a period of time that exceeds 1 second.

7. A method as recited in claim 5 wherein exposing the dental material in step (c) is performed for a period of time that is at least 20% of the total time that the dental material is exposed to the light.

8. A method as recited in claim 5 wherein exposing the dental material in step (c) is performed for a period of time that is up to about 40% of the total time that the dental material is exposed to the light.

9. A method as recited in claim 5 wherein increasing and exposing of step (d) are performed for at least half of the time that the dental material is exposed to the light.

10. A method as recited in claim 5 wherein increasing and exposing of step (d) are performed for more than about 3 seconds.

11. A method as recited in claim 5 wherein said second power level is at least twice the power of said first power level.

12. A method for obtaining a cured a polymeric dental composite, the dental composite including monomers and at least one initiator sensitive to light energy at wavelength L, the method comprising the steps of:

(a) using a light source to generate light energy at about wavelength L, (b) directing said light energy at a first high energy level toward the dental composite so that said light energy causes the initiator to begin polymerization of monomers of the dental composite into polymers, (c) decreasing the energy level of light energy directed toward the dental composite until the light energy reaches a second lower energy level, (d) increasing the energy level of light energy directed toward the dental composite.

13. A method as recited in claim 12 wherein said first energy level is about 250 milliwatts.

14. A method as recited in claim 12 wherein said second energy level is about 50 milliwatts.

15. A method as recited in claim 12 wherein said second energy level is about 20% or more of said first energy level.

16. A method as recited in claim 12 wherein said decreasing step (c) is performed over a period of time that is less than about 30% of the total time that light energy is exposed to said dental composite.

17. A method as recited in claim 12 wherein the time utilized to perform step (d) is greater than the time utilized to perform step (c).

18. A method as recited in claim 12 wherein said step (d) is performed until the light energy reaches a third power level, said third power level being greater than said first power level.

19. A method as recited in claim 18 wherein said third power level is less than or equal to said first power level.

20. A method for obtaining a cured a dental material comprising:

(a) applying light energy of wavelength L to a dental material which is sensitive to and polymerizes when exposed to said light energy, said light energy being applied at a first power level P1, (b) maintaining application of light energy to the dental material at a power level about P1 for a brief period, (c) while continuing to apply light energy to the dental material, quickly decreasing the light energy power level to a level P2, where $P2<P1$, (d) maintaining application of light energy to the dental material about P2 until the dental material is sufficiently cured for its intended purpose.

21. A method as recited in claim 20 wherein said P2 is not more than half of P1.

22. A method for polymerizing a restorative dental material, the method comprising:

(a) selecting a restorative dental material, (b) selecting a light source capable of causing polymerization of said restorative dental material, (c) applying energy from said light source to said restorative dental material, (d) modulating said energy according to a sine function so that the energy level to which said restorative dental material is exposed repeatedly increases and decreases during the polymerization process.

23. A method as recited in claim 22 wherein said modulating step (d) is performed within a first energy level E1 and a second energy level E2, E1 being at least twice the energy of E2.

24. A method as recited in claim 22 wherein said modulating step (d) is performed within a first energy level E1 and a second energy level E2, E1 being at least four times the energy of E2.

25. A method as recited in claim 22 wherein said modulating step (d) is performed between a first energy level E1 and a second energy level E2, and wherein said applying step (c) is initiated at a third energy level E3 where $E1>E3>E2$.

26. A method for curing a dental material comprising:

(a) selecting a light source capable of causing polymerization of the dental material, (b) directing light energy on the dental material for a period of time T1 at a constant power level P1, (c) discontinuing step (b) for a rest period T2, (d) directing light energy on the dental material for a period of time T3 at a constant power level P2.

27. A method as recited in claim 26 wherein T1 is approximately equal to T3.

28. A method as recited in claim 26 wherein T2 is not equal to T1 and T2 is not equal to T3.

29. A method as recited in claim 26 where P1 is less than P2.

30. A method as recited in claim 26 wherein P2 is approximately five times P1.

31. A method as recited in claim 26 wherein T2 is at least about three times as long as T1.

32. A method for obtaining a cured a dental composite comprising the steps of:

(a) exposing the dental composite to light energy of a wavelength appropriate to cause curing of the dental composite for a brief period of time at a constant initial power level, (b) continuing to expose the dental composite to the light energy while gradually increasing the power level to a level that is a multiple of at least 2 of the initial power level, (c) permitting the dental composite to cure by polymerization initiated and carried out by the light energy.

33. A method for obtaining a cured a dental material comprising:

(a) obtaining a dental material which cures when exposed to light of a wavelength L, (b) obtaining a light source which produces light of wavelength L, (c) exposing said dental material to said light for a first period of time at a first constant power level, (d) exposing said dental material to said light for a second period of time while said power level is increased from said first power level to a second power level, said third power level being greater than said first power level, (e) exposing said dental material to said light for a third period of time with power constant at said third power level during said third period of time.

34. A method as recited in claim 33 wherein said first period of time is greater than said second period time and said first period of time is greater than said third period of time.

35. A method as recited in claim 34 wherein said second power level is double or more said first power level.

36. A method for curing a polymeric composite obtaining a cured polymeric dental composite comprising the steps of:

a. exposing the composite to a light source at a constant high power level for at least 1 second to initiate polymerization of the composite, b. precipitously decreasing power of the light source to a significantly lower level in a brief time period, c. gradually increasing power of the light source over a longer time period to carry out polymerization of the composite, d. terminating power to the light source when sufficient light exposure time has passed for polymerization of the composite to be substantially completed.

37. A method for obtaining a cured dental composite that includes monomers and an initiator comprising the steps of:

a. providing power to a light source of a wavelength to which the initiator is sensitive, the initial power level being high, b. maintaining said high initial power level for a period of time while exposing the composite to light from the light source, c. incrementally decreasing power to said light source by a small amount and maintaining power at said lower level for a period of time while exposing the composite to light from the light source, d. repeating step (c) at least twice, e. decreasing power to a final power level that is lower than any of the power levels in steps (a) and (c) above, f. maintaining power at said final power level for a period of time longer than any of said periods of time in steps (a) and (c) above, g. exposing light from the light source to the composite during step (f) above.

38. A method for obtaining a polymerized polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material at a first high power level, e. gradually decreasing intensity of light from said light source over time until said polymeric material has endured enough exposure to said light for polymerization of said polymeric material to continue to substantial completion.

39. A method for obtaining a polymerized polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material at a first low power level, e. gradually increasing intensity of light from said light source over time until said polymeric material has endured enough exposure to said light for polymerization of said polymeric material to continue to substantial completion.

40. A method for obtaining a polymerized polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material in a pattern of modulated light intensity, the modulation of light intensity being performed according to a waveform that is selected from the group consisting of sine waves, square waves, triangular waves, and discontinuous waves, e. continuing exposing said polymeric material to said modulated light until said polymeric material has endured enough exposure to said light for polymerization of said polymeric material to continue to substantial completion.

41. A method for obtaining a cured polymeric dental material comprising the steps of:

a. selecting a quantity of polymeric material, b. selecting a light source capable of polymerizing said polymeric material, c. exposing light from said light source to said polymeric material at a first low power level, d. rapidly increasing the intensity of said light to a second high power level, e. rapidly decreasing the intensity of said light to a third low power level that is approximately equal to said first low power level such that the waveform of light intensity of steps (c), (d) and (e) is a triangular wave, and f. repeating steps (c), (d) and (e) until polymerization of said polymeric material is substantially complete.

42. A method for obtaining a polymerized polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material at a first high power level, e. permitting said polymeric material to cure.

43. A method for obtaining a cured composite dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material in a square waveform, e. permitting said polymeric material to cure.

44. A method for obtaining a cured polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material according to a triangular waveform, e. permitting said polymeric material to cure.

45. A method for obtaining a cured polymeric dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material according to a curved waveform, e. permitting said polymeric material to cure.

46. A method for obtaining a cured dental material comprising the steps of:

a. selecting a quantity of polymeric material, b. placing said polymeric material in a location where it is to be utilized, c. selecting a light source capable of initiating polymerization of said polymeric material, d. exposing light from said light source to said polymeric material at an instantaneous high power level, e. terminating exposure of light to said polymeric material, f. waiting for a rest period during which said polymeric material is not exposed tolight from said light source, g. repeating steps (d) and (e) above, h. permitting said polymeric material to cure.

47. A method for obtaining a cured polymeric dental material comprising the steps of:

a. selecting a quantity of polymeric material that includes monomers and a plurality of initiators being sensitive to light of various wavelengths, b. selecting light sources that include wavelengths of light to which said initiators are sensitive, c. exposing light from a first light source to said polymeric material according to a light source power modulation scheme so that an initiator sensitive to light from said first light source will cause polymerization of monomers into polymers to begin, d. exposing light from a second light source having a wavelength different than the wavelength of said first light source to said polymeric material according to a light source power modulation scheme so that an initiator sensitive to light from said second light source will cause polymerization of monomers into polymers, e. permitting said polymeric material to cure.

* * * * *